(12) United States Patent
Kong et al.

(10) Patent No.: US 12,616,597 B1
(45) Date of Patent: May 5, 2026

(54) NASAL DILATING DEVICE

(71) Applicant: Fissiontech LLC, New York City, NY (US)

(72) Inventors: Xiangyun Kong, Philadelphia, PA (US); Christopher John Baton, Dover Plains, NY (US)

(73) Assignee: FISSIONTECH LLC, New York City, NY (US)

( * ) Notice: Subject to any disclaimer, the term of this patent is extended or adjusted under 35 U.S.C. 154(b) by 0 days.

(21) Appl. No.: 19/295,482

(22) Filed: Aug. 8, 2025

Related U.S. Application Data

(60) Provisional application No. 63/797,798, filed on Apr. 30, 2025.

(51) Int. Cl.
A61M 21/02 (2006.01)
A61F 5/08 (2006.01)

(52) U.S. Cl.
CPC ..................................... A61F 5/08 (2013.01)

(58) Field of Classification Search
CPC ........ A61F 5/08; A61F 13/58; A61F 13/8405; A61M 21/02; A61M 11/04; B29C 64/393
See application file for complete search history.

(56) References Cited

U.S. PATENT DOCUMENTS

| | | | | |
|---|---|---|---|---|
| 2008/0119885 | A1* | 5/2008 | Yazdi | A61F 5/08 606/199 |
| 2009/0099566 | A1* | 4/2009 | Maness | A61F 2/4607 606/62 |
| 2014/0296904 | A1* | 10/2014 | Andre | A61F 5/56 606/199 |
| 2021/0085509 | A1* | 3/2021 | Magness | B29C 64/393 |
| 2024/0016650 | A1* | 1/2024 | Hagerty | A61F 13/58 |

FOREIGN PATENT DOCUMENTS

| | | | | | |
|---|---|---|---|---|---|
| CN | 114376782 | A | * | 4/2022 | A61F 5/08 |

* cited by examiner

*Primary Examiner* — Tuan V Nguyen
(74) *Attorney, Agent, or Firm* — Gallium Law; Jacob Panangat; Justin Schwechter

(57) ABSTRACT

Included in the present disclosure is a device, including a bridge having a first end and a second end opposite the first end. In some embodiments, the device includes a first arm detachably coupled to the first end. According to some embodiments, the device includes a second arm detachably coupled to the second end. The device may be configured to detachably couple with a nose of a user.

20 Claims, 29 Drawing Sheets

30

602

604

30

30

1100

1100

1102

1104

1100

1106

1100

1110

1108

NASAL DILATING DEVICE

CROSS-REFERENCE TO RELATED APPLICATIONS

The entire contents of the following application are incorporated herein: U.S. Provisional Patent Application No. 63/797,798; filed on Apr. 30, 2025; and entitled NASAL DILATING DEVICE.

FIELD OF TECHNOLOGY

The present disclosure relates to devices for opening nasal airways.

BACKGROUND

Nasal dilators help to keep a person's nasal passages open in order to facilitate their breathing. This may include times when deeper breaths are taken, such as during sleep or exercise. Many nasal dilators operate by physically widening the nostrils or the nasal valve area, which is the narrowest part of the nasal airway.

Nasal dilators are generally used in order to reduce snoring, improve airflow during sleep, helping with problems such as mild sleep apnea or nasal congestion, and to help with athletic performance through easing nasal breathing.

SUMMARY

Included in the present disclosure is a device, including a bridge having a first end and a second end opposite the first end. In some embodiments, the device includes a first arm detachably coupled to the first end. According to some embodiments, the device includes a second arm detachably coupled to the second end. The device may be configured to detachably couple with a nose of a user.

In some embodiments, the first end of the bridge includes a first insert. According to some embodiments, the second end of the bridge comprises a second insert. The first insert may include a first female coupling mechanism. In some embodiments, the second insert includes a second female coupling mechanism.

According to some embodiments, the first end includes a first female coupling mechanism. The second end may include a second female coupling mechanism. In some embodiments, the bridge is configured to change in width by about five millimeters when in use. According to some embodiments, the bridge includes a spring constant configured to apply pressure to nostrils of the nose to thereby open a nasal airway. The bridge may include i) stainless steel, ii) high-precision phosphorus copper, iii) titanium, iv) polymer, v) polycarbonate, vi) steel, or vii) combinations thereof.

In some embodiments, the first arm includes a first slot. According to some embodiments, the second arm comprises a second slot. The first slot may be configured to detachably couple with the first insert. In some embodiments, the second slot is configured to detachably couple with the second insert. According to some embodiments, the first slot is configured to detachably couple with the first end. The second slot may be configured to detachably couple with the second end.

In some embodiments, the device further includes a first male coupling mechanism disposed within the first slot. According to some embodiments, the device further includes a second male coupling mechanism disposed within the second slot. The first male coupling mechanism may be configured to detachably couple with the first female coupling mechanism when the first slot is coupled with the first insert or first end. In some embodiments, the second male coupling mechanism is configured to detachably couple with the second female coupling mechanism when the second slot is coupled with the second insert or second end. According to some embodiments, the first arm and the second arm each include i) silicon, ii) plastic, iii) polymer, or iv) combinations thereof.

The first arm may include a first nasal coupling mechanism. In some embodiments, the second arm includes a second nasal coupling mechanism. According to some embodiments, the first nasal coupling mechanism is configured to detachably couple the first arm to a first ala of the nose. The second nasal coupling mechanism may be configured to detachably couple the second arm to a second ala of the nose. In some embodiments, the device further includes a first pair of magnets disposed in the first nasal coupling mechanism, the first pair of magnets configured to detachably couple the first arm to the first ala. According to some embodiments, the device includes a second pair of magnets disposed in the second nasal coupling mechanism, the second pair of magnets configured to detachably couple the second arm to the second ala.

The device may be configured to apply pressure to nostrils of the nose, thereby opening a nasal airway. In some embodiments, the bridge includes a bridge position indicator, the first arm includes a first arm position indicator, and the second arm includes a second arm position indicator. According to some embodiments, the bridge position indicator and the first arm position indicator are configured to align the bridge with the first arm. The bridge position indicator and the second arm position indicator may be configured to align the bridge with the second arm. In some embodiments, i) the bridge position indicator, ii) the first arm position indicator, iii) the second arm position indicator, or iv) combinations thereof are triangular.

According to some embodiments, the arm includes an arm size indicator. The bridge includes a bridge size indicator. A height of the bridge may be from 6.667 millimeters (mm) to 9.6 mm. In some embodiments, a width of the bridge, less the first insert and the second insert, is from 20.458 mm to 35.112 mm. According to some embodiments, a width of i) the first insert, ii) the second insert, or iii) both is from 4.167 mm to 6 mm. A height of i) the first insert, ii) the second insert, or iii) both may be from 4.583 mm to 6.6 mm.

In some embodiments, a depth of the arm is from 9.008 mm to 13.524 mm. According to some embodiments, a height of an inner portion of the arm is from 12.983 mm to 20.592 mm. A width of an ala contacting portion of the arm may be from 6.75 mm to 9.72 mm. In some embodiments, an angle of travel of the bridge is from 80 degrees to 144 degrees.

Also included in the present disclosure is a system including a device as described above. In some embodiments, the system includes a case including an interior, the case sized and configured to hold the device within the interior.

According to some embodiments, the case includes i) plastic, ii) foam, iii) faux fur, iv) nylon, or v) combinations thereof. The plastic may include i) transparent plastic, ii) translucent plastic, iii) opaque plastic, iv) colored plastic, or v) combinations thereof.

In some embodiments, a height of the case is from 20.758 mm to 29.892 mm. According to some embodiments, a length of the case is from 59.608 mm to 85.836 mm. A width of the case may be from 34.675 mm to 49.932 mm.

Also included in the present disclosure is a kit, including a first device as described above, the first device including a first bridge, a first arm, and a second arm. The kit may include a second device as described above, the second device including a second bridge, a third arm, and a fourth arm.

In some embodiments, the first bridge includes a first width. According to some embodiments, the second bridge includes a second width. The first width may be different than the second width.

In some embodiments, the first bridge includes a first material. According to some embodiments, the second bridge includes a second material. The first material may be different than the second material.

In some embodiments, the first bridge includes a first spring constant. According to some embodiments, the second bridge includes a second spring constant. The first spring constant may be different than the second spring constant.

In some embodiments, the first arm includes a first nasal coupling mechanism defining a first width. According to some embodiments, the second arm includes a second nasal coupling mechanism defining a second width. The third arm may include a third nasal coupling mechanism defining a third width. In some embodiments, the fourth arm includes a fourth nasal coupling mechanism defining a fourth width. According to some embodiments, the first width and the second width are the same. The third width and the fourth width may be the same. In some embodiments, the first width and the second width are different from the third width and the fourth width.

According to some embodiments, the first arm includes a first nasal coupling mechanism configured to be inserted into a nostril a first depth. The second arm may include a second nasal coupling mechanism configured to be inserted into a nostril a second depth. In some embodiments, the third arm includes a third nasal coupling mechanism configured to be inserted into a nostril a third depth. According to some embodiments, the fourth arm includes a fourth nasal coupling mechanism configured to be inserted into a nostril a fourth depth. The first depth and the second depth may be the same. In some embodiments, the third depth and the fourth depth are the same. According to some embodiments, the first depth and the second depth are different from the third depth and the fourth depth.

The first arm may include a first material. In some embodiments, the second arm includes a second material, the third arm includes a third material, and the fourth arm includes a fourth material. According to some embodiments, the first material and the second material are the same, The third material and the fourth material may be the same. In some embodiments, the first material and the second material are different from the third material and the fourth material.

According to some embodiments, the kit further includes a case including an interior, the case sized and configured to hold the first device and the second device within the interior. The case may include i) plastic, ii) foam, iii) faux fur, iv) nylon, or v) combinations thereof. In some embodiments, the plastic includes i) transparent plastic, ii) translucent plastic, iii) opaque plastic, iv) colored plastic, or v) combinations thereof.

According to some embodiments, a height of the case is from 20.758 mm to 29.892 mm. A length of the case may be from 59.608 mm to 85.836 mm. In some embodiments, a width of the case is from 34.675 mm to 49.932 mm.

The foregoing, and other features and advantages of the invention, will be apparent from the following, more particular description of the preferred embodiments of the invention, the accompanying drawings, and the claims.

BRIEF DESCRIPTION OF DRAWINGS

These and other features, aspects, and advantages are described below with reference to the drawings, which are intended to illustrate, but not to limit, the invention. In the drawings, like characters denote corresponding features consistently throughout similar embodiments.

DETAILED DESCRIPTION OF THE INVENTION

External nasal dilators physically attach to a person's nose along an exterior portion of the nose. These external nasal dilators traditionally use magnets or adhesive(s) in order to pull upon the nostrils, thereby opening the nasal airway. However, such devices include multiple shortcomings that the present disclosure serves to resolve.

For example, devices using adhesive are single-use and must be disposed of each time the device is used. Devices using magnets also include adhesive(s) in order to adhere the magnet to a person's nose. Additionally, in order for the adhesive to be effective, the person must thoroughly wash the location to which they are going to stick the adhesive prior to each use. Finally, these prior devices are "one-size-fits-all" in that there are no customization options available.

Disclosed herein, in some aspects, is a nasal dilating device configured to couple with a user's nose to dilate one or more nasal airways and/or nostrils. The device of the present disclosure may be modular, including two arms that interact with a person's nose, as well as a bridge that connects the two arms. Multiple size, depth, and material options may be made available to the user, permitting the user to customize their experience, such as by way of how deep the arms enter the person's nose, how long the bridge is, how stiff the bridge is, and how soft the arms are. Additionally, because adhesive may not be necessary, the device may be reusable, instead of a one-time-use device. Moreover, there may be no disposable components in the device of the present disclosure, meaning fewer items going into the trash, and fewer purchases needing to be made by the user.

Throughout the present disclosure, reference may be made to a "kit." This "kit" may include any number of bridges and arms with any variety of features for providing a customizable, modular experience to the user.

Figure 1:
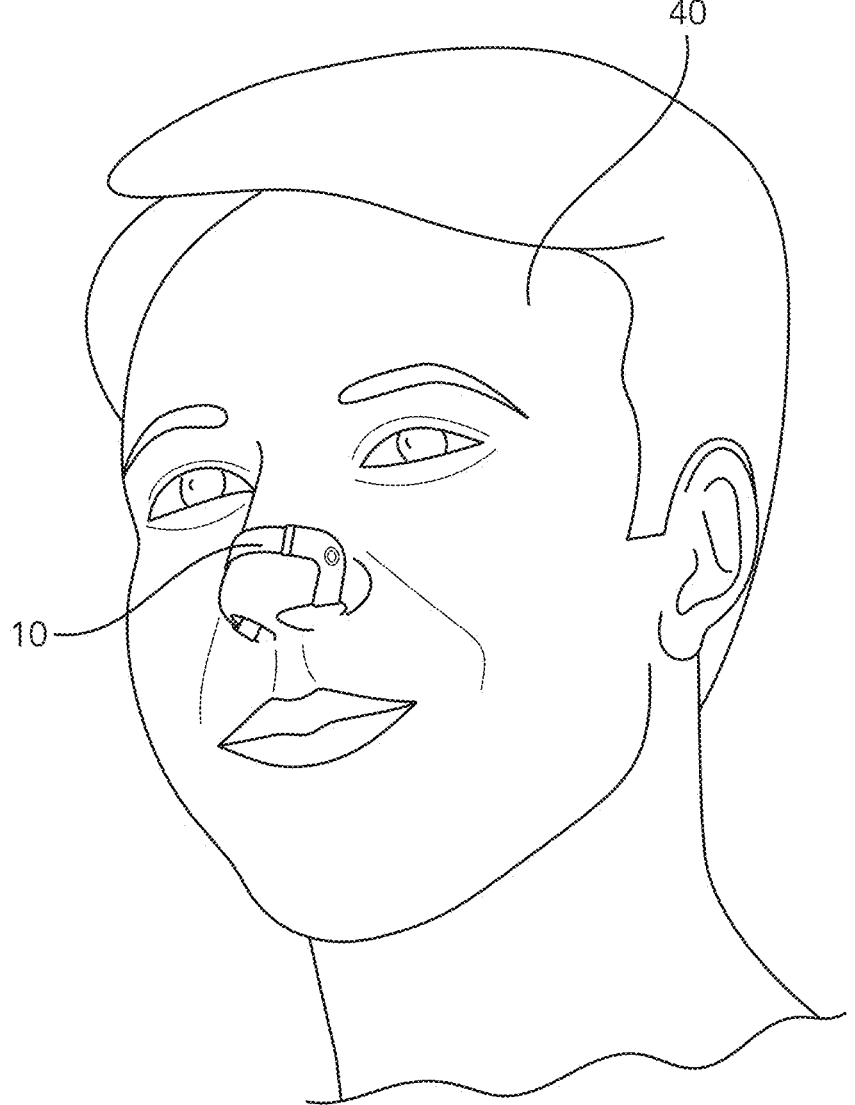
FIG. 1 illustrates a user using a nasal dilating device, according to some embodiments.

FIG. 1 illustrates a user 40 using a nasal dilating device 10, according to some embodiments. The nasal dilating device 10 may partially insert into one of the user's 40 nostrils, wrap around the ala of the user's 40 nose, across/around the dorsum of the user's 40 nose, wrap around the ala on the opposite side of the user's 40 nose, and/or partially insert into the other user's nostril. In application, the entire nasal dilating device 10 may be inserted into both of the user's 40 nostrils at the same time.

Figure 2:
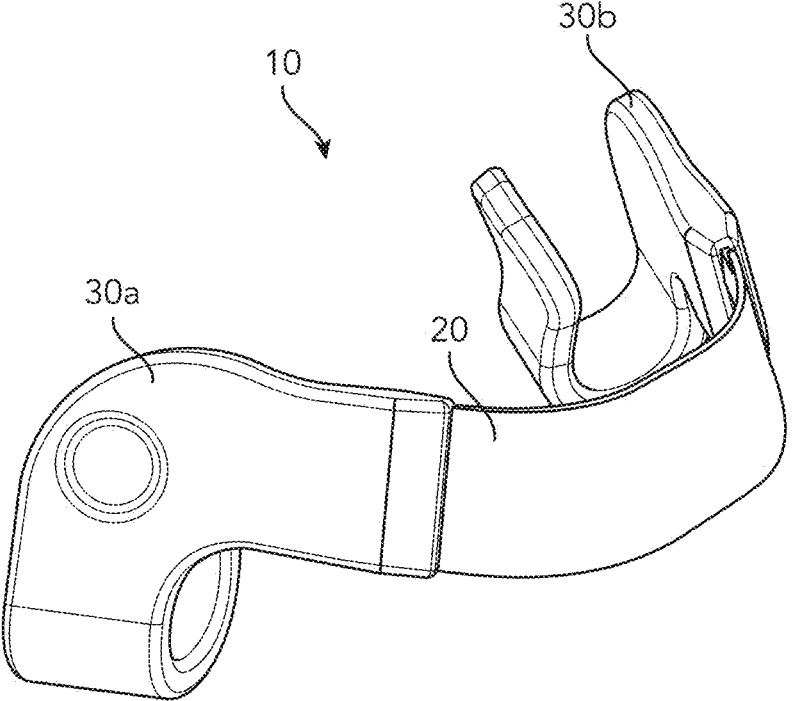
FIG. 2 illustrates a perspective view of a nasal dilating device, according to some embodiments.
Figure 3A:
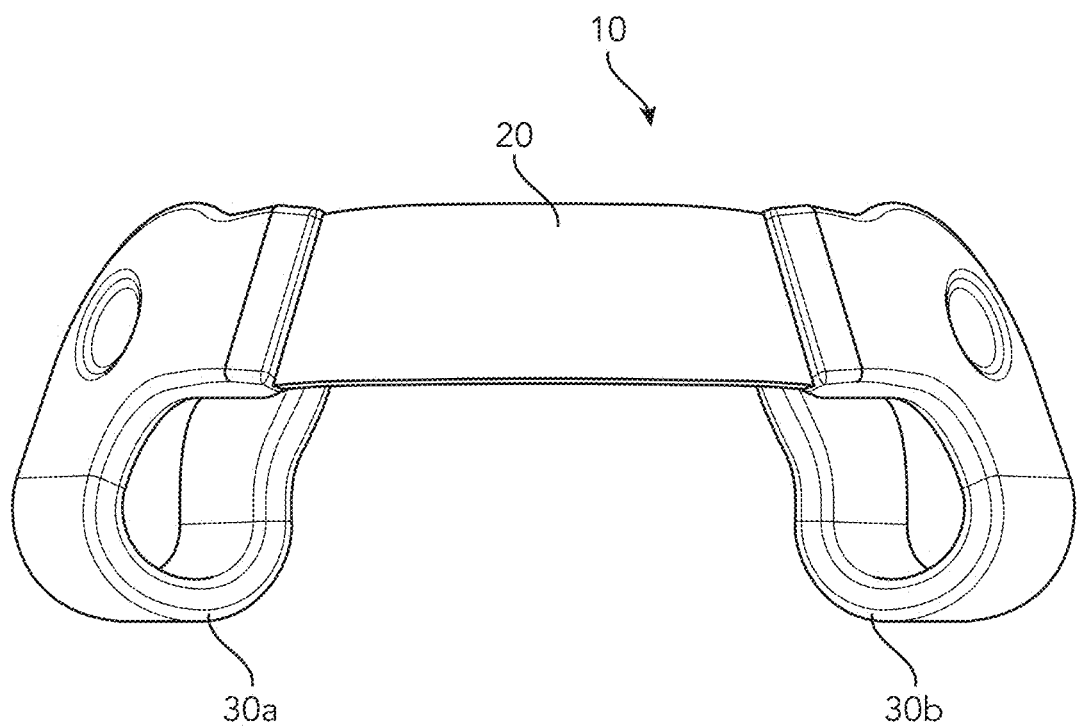
FIG. 3A illustrates a front view of the nasal dilating device of FIG. 1, according to some embodiments.
Figure 3B:
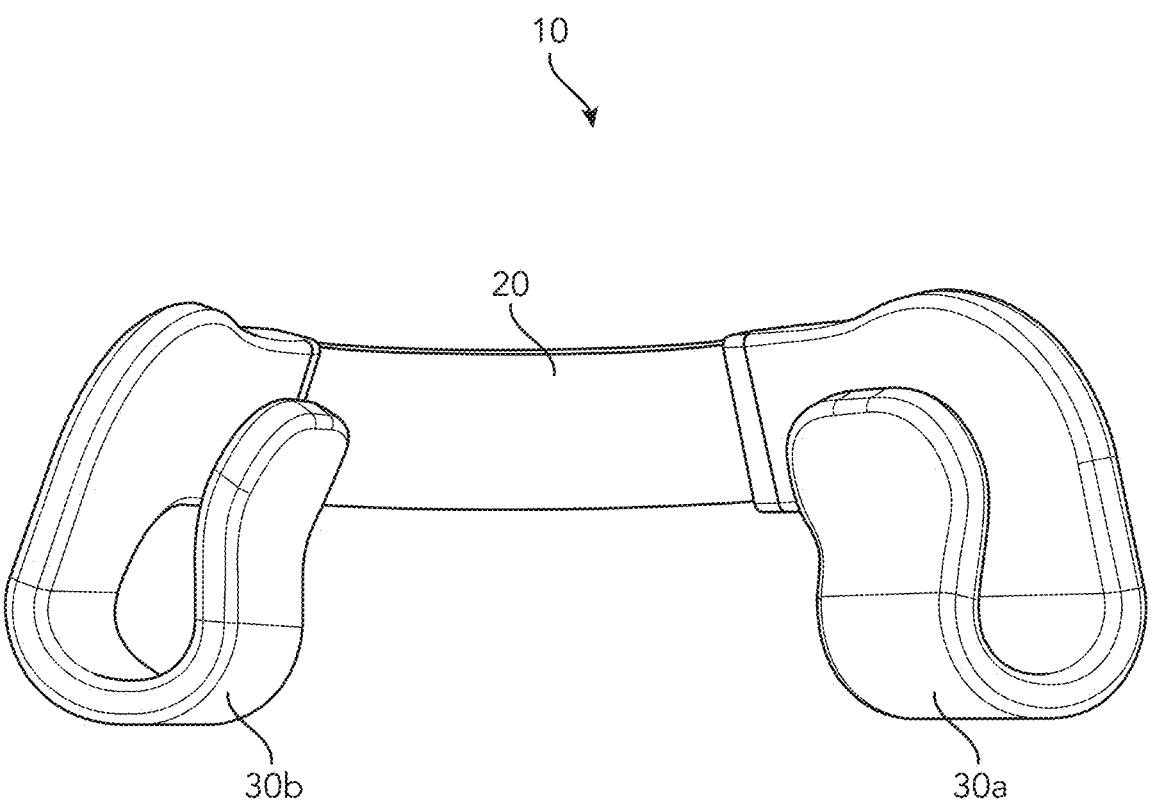
FIG. 3B illustrates a back view of the nasal dilating device of FIG. 1, according to some embodiments.
Figure 3C:
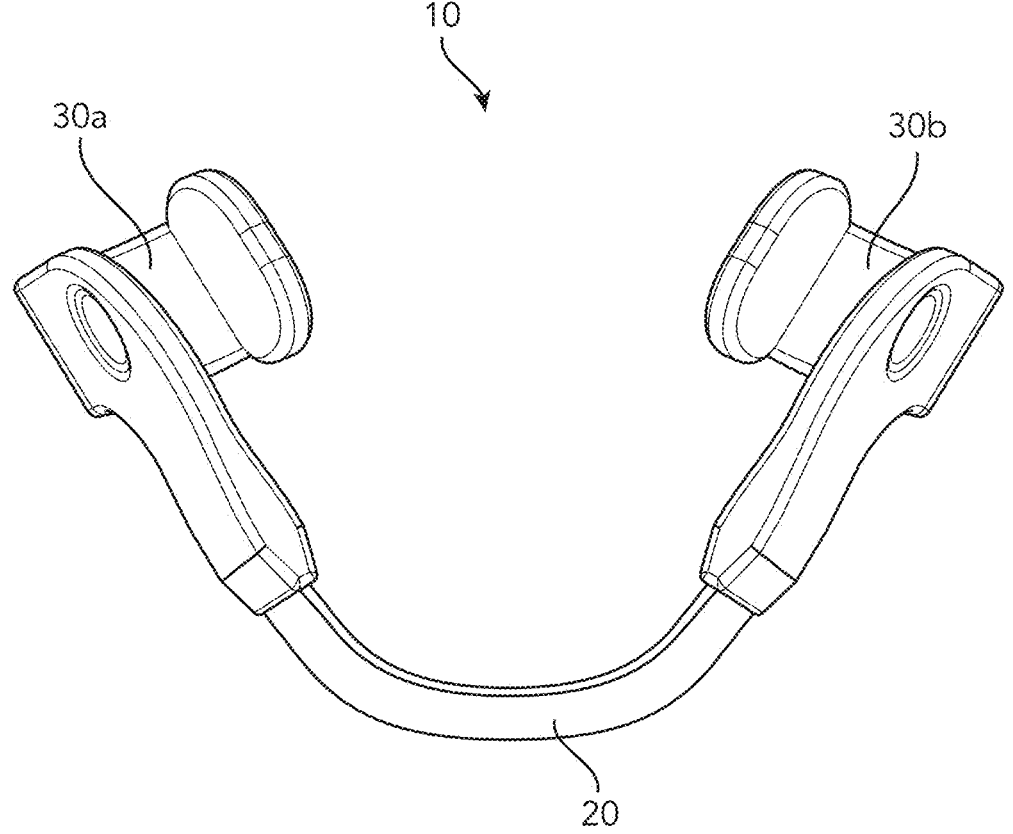
FIG. 3C illustrates a top view of the nasal dilating device of FIG. 1, according to some embodiments.
Figure 3D:
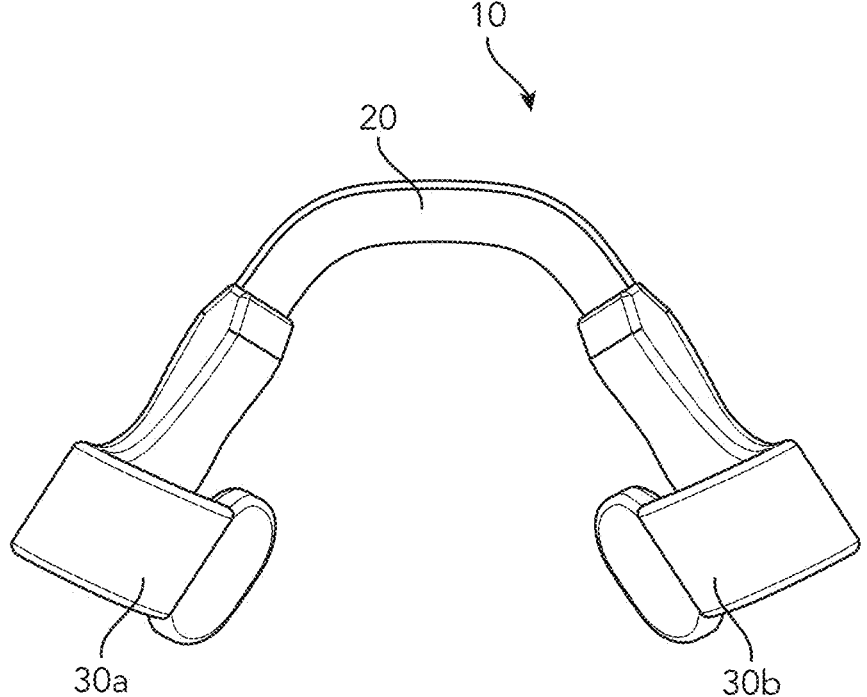
FIG. 3D illustrates a bottom view of the nasal dilating device of FIG. 1, according to some embodiments.
Figure 3E:
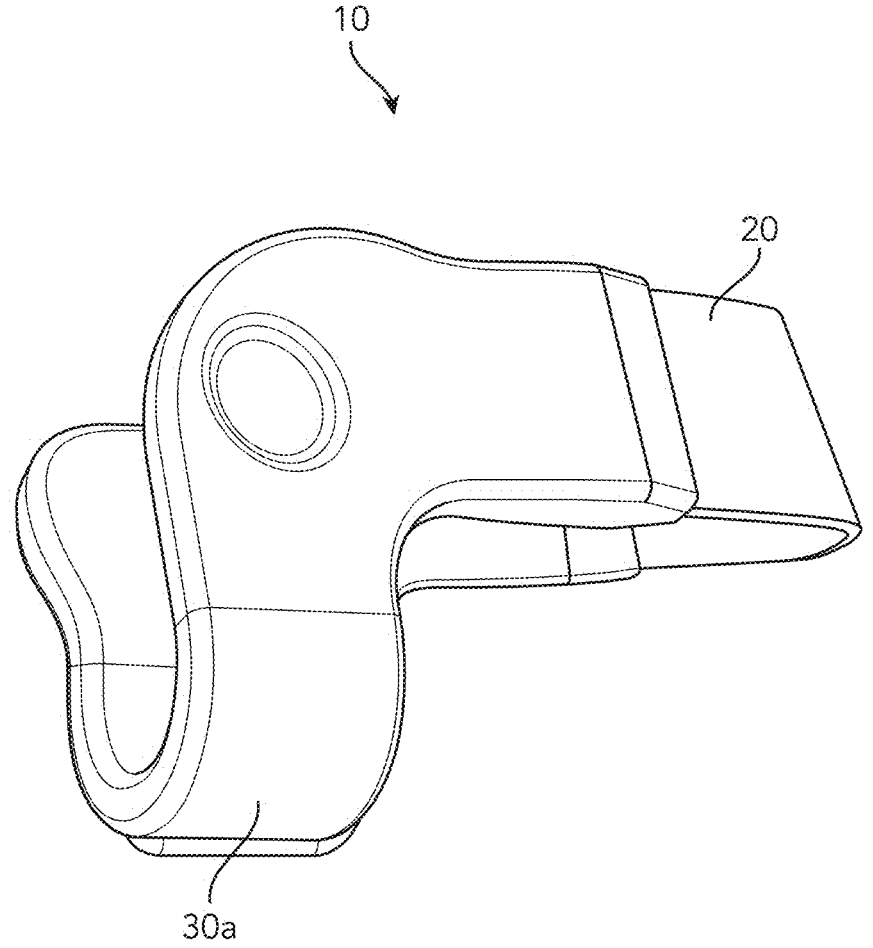
FIG. 3E illustrates a side view of the nasal dilating device of FIG. 1, according to some embodiments.

FIG. 2 illustrates a perspective view of a nasal dilating device 10, according to some embodiments. FIG. 3A illustrates a front view, FIG. 3B illustrates a back view, FIG. 3C illustrates a top view, FIG. 3D illustrates a bottom view, FIG. 3E illustrates a side view, FIG. 4A illustrates a front exploded view, FIG. 4B illustrates a back exploded view, and FIG. 4C illustrates a top exploded view of the nasal dilating device 10.

As shown in FIGS. 2-4C, the nasal dilating device 10 includes a bridge 20, a first arm 30*a*, and a second arm 30*b* on either side of the bridge 20. The first arm 30*a* and the second arm 30*b* may be detachable from the bridge 20. As described below with respect to the specific components, variations of the bridge 20 and the arms 30 may be provided in order to best match up with a nose of a given user onto which the nasal dilating device 10 is being placed. Such modular customization of the nasal dilating device may facilitate comfort for the user.

Figure 4A:
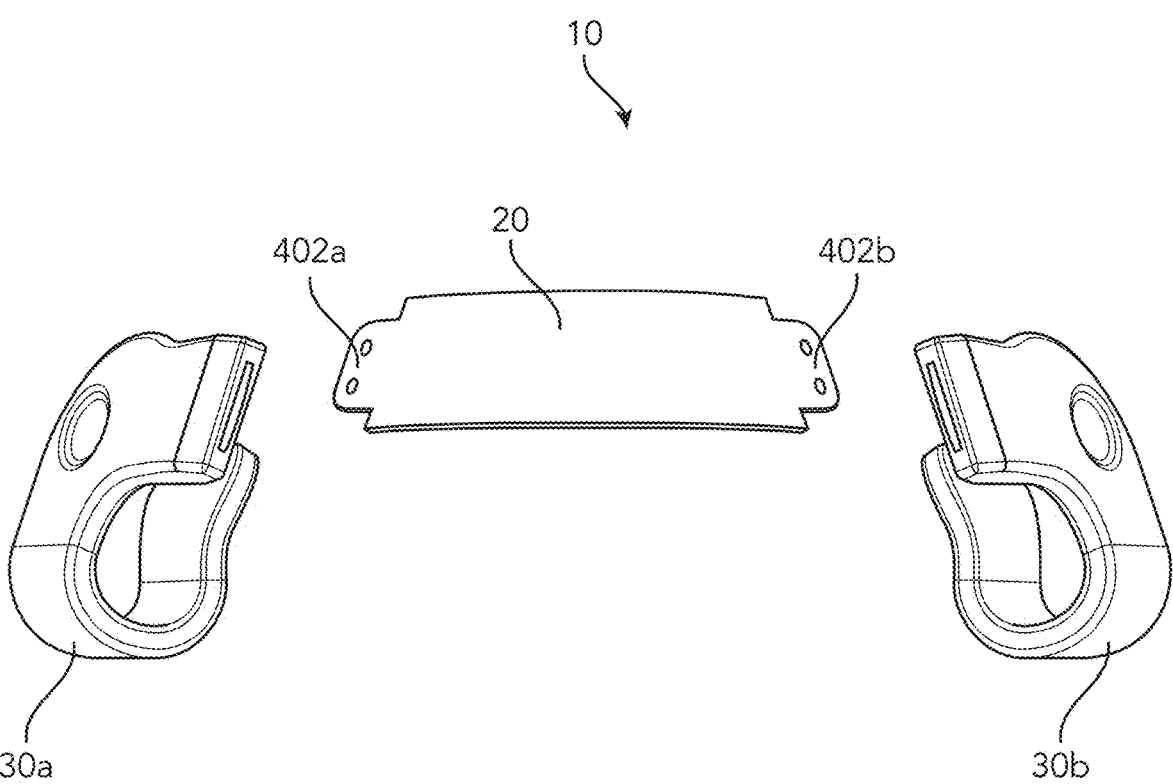
FIG. 4A illustrates a front exploded view of the nasal dilating device of FIG. 1, according to some embodiments.
Figure 4B:
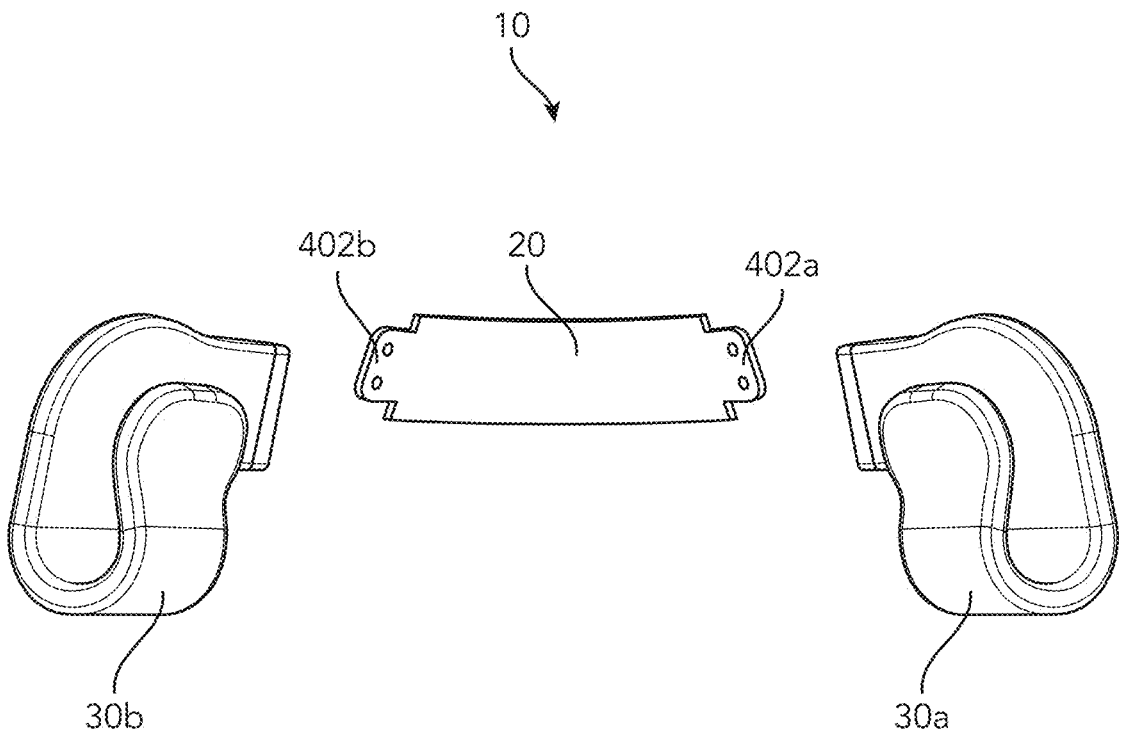
FIG. 4B illustrates a back exploded view of the nasal dilating device of FIG. 1, according to some embodiments.
Figure 4C:
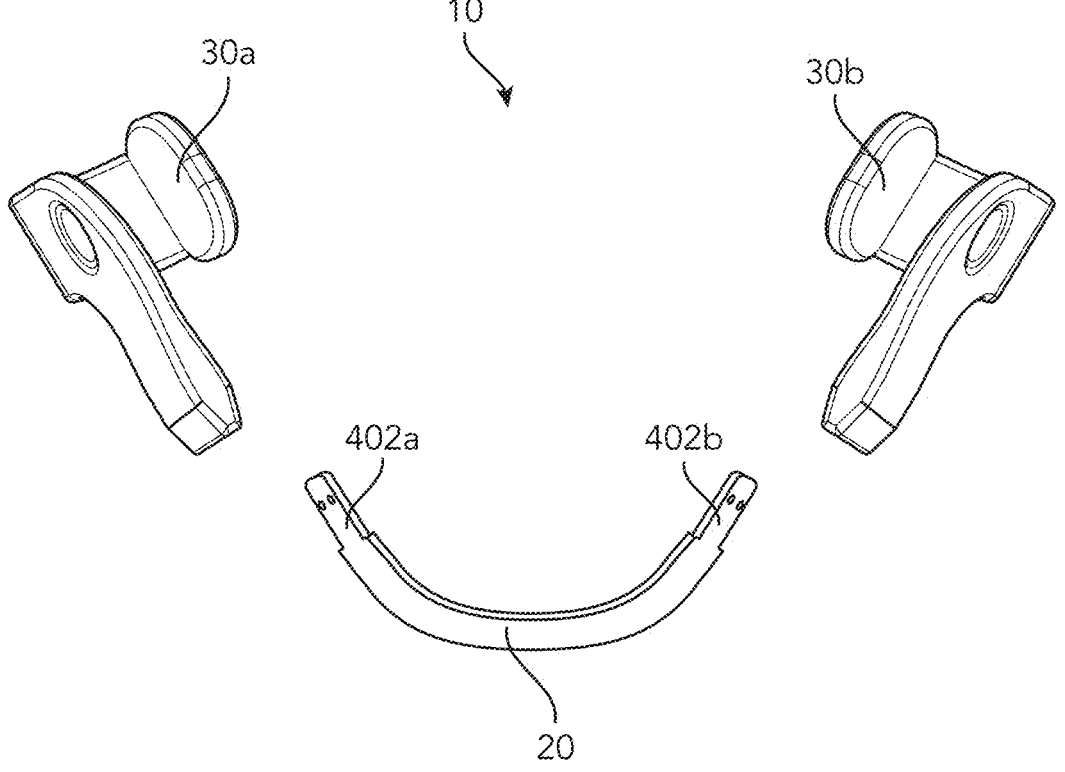
FIG. 4C illustrates a top exploded view of the nasal dilating device of FIG. 1, according to some embodiments.

As seen in FIGS. 4A-4C, the bridge 20 may include inserts 402 for coupling to slots in arms 30 (not labeled here, but see e.g., 604 in FIGS. 6A-6D). These inserts 402 may be of a height and length which interact with the slots of the arms 30, such as to make a strong coupling, while not detracting from the ability to remove the arms 30 from the bridge 20. As also shown in FIGS. 4A-4C, the bridge includes an insert 402*a* on one side of the bridge 20, and an insert 402*b* on a side of the bridge 20 opposite the insert 402*a*. Insert 402*a* may align and/or be configured to couple to arm 30*a*, and insert 402*b* may align and/or be configured to couple to arm 30*b*.

Figure 5A:
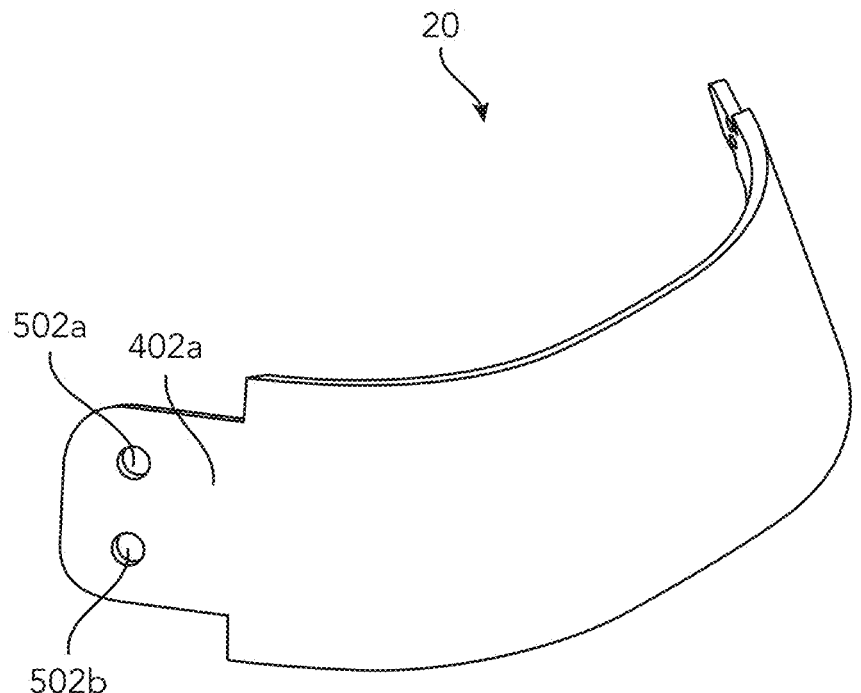
FIG. 5A illustrates a perspective view of a bridge, according to some embodiments.
Figure 5B:
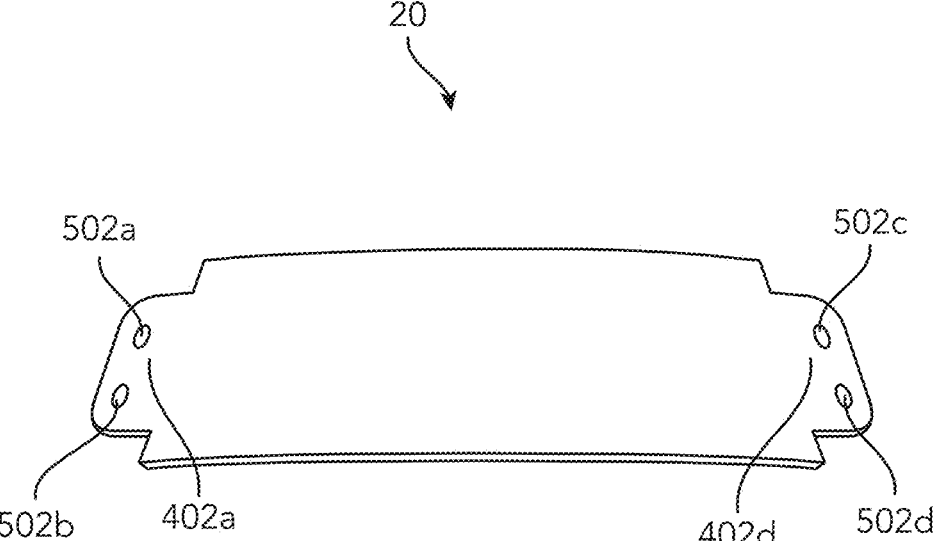
FIG. 5B illustrates a front view of the bridge of FIG. 5A, according to some embodiments.
Figure 5C:
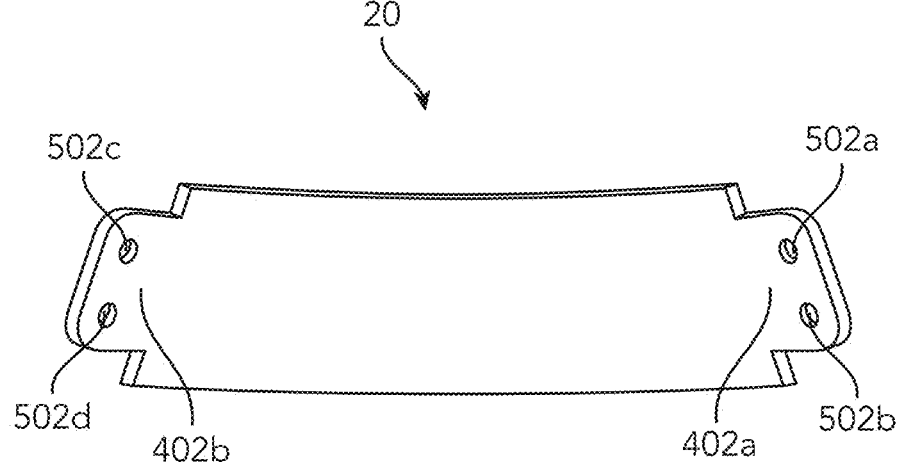
FIG. 5C illustrates a back view of the bridge of FIG. 5A, according to some embodiments.
Figure 5D:
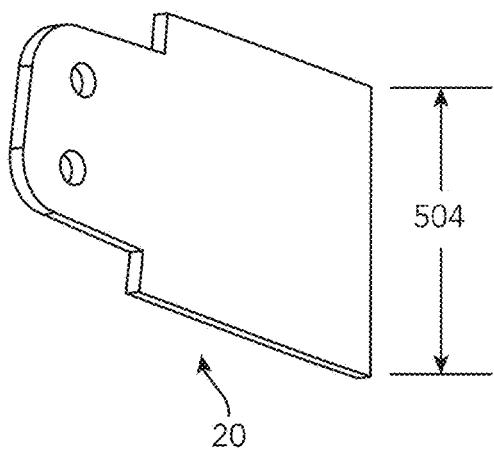
FIG. 5D illustrates a diagrammatic side view of the bridge of FIG. 5A, according to some embodiments.
Figure 5E:
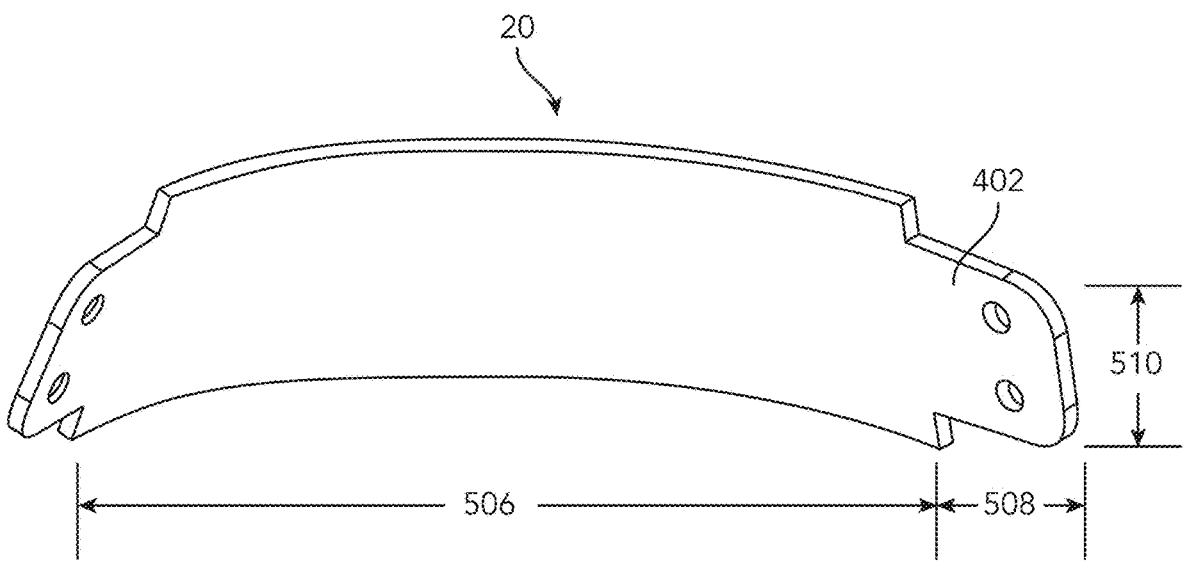
FIG. 5E illustrates a diagrammatic back view of the bridge of FIG. 5A, according to some embodiments.

FIG. 5A illustrates a perspective view of a bridge 20, according to some embodiments. FIG. 5B illustrates a front view and FIG. 5C illustrates a back view thereof. FIG. 5D illustrates a diagrammatic side view, and FIG. 5E illustrates a diagrammatic back view thereof. As shown in FIGS. 5A-5C, the bridge 20 may include female coupling mechanisms 502 disposed about the insert 402. The female coupling mechanisms 502 may be holes or recessed portions disposed within the insert 402.

As shown in FIGS. 5A-5C, two female coupling mechanisms 502*a* and 502*b* are disposed within insert 402*a*, and two female coupling mechanisms 502*c* and 502*d* are disposed within insert 402*b*. In alternate embodiments, one female coupling mechanism 502 is disposed within each insert 402. In further embodiments, a greater number than two female coupling mechanisms 502 are disposed within each insert 402. In still further embodiments, the number of female coupling mechanisms 502 disposed within insert 402*a* does not match the number of female coupling mechanisms 502 disposed within insert 402*b*.

The bridge 20 may include a height and a width. The height and width of the bridge 20 may be sized and/or configured to facilitate interaction with a user's dorsum (i.e., the bridge of a user's nose). In embodiments including a kit, multiple bridges 20 may be included, the bridges 20 having different heights and/or widths from one another. In this way, the user may select a bridge 20 having a height and a width that match or at least substantially match the size and/or shape of the user's nose. In some embodiments, the bridge experiences about five millimeters in length change while in use. According to some embodiments, the bridge includes a spring constant configured to apply pressure to the nostrils in order to open the nasal airway. In embodiments including a kit, different bridges may include different changes in length during use, and/or different spring constants. For example dimensions of the bridge 20, refer to FIGS. 5D and 5E below.

The device may be used by compressing (e.g., bending) the bridge, at least partially, such that the arms may be inserted about a user's alae. Once the arms are secured to the user's alae, the tension in the bridge due to the bridge's inherent spring constant will attempt to bring the bridge back to its original position, outside of external force. This tension in the bridge will cause the arms to separate the alae, along with further portions of the nostril, away from the septum, thereby opening the nasal cavity. This, in turn, may facilitate the opening of the nasal airway, easing air passage through this nasal airway.

The bridge may be formed from stainless steel, high-precision phosphorus copper, titanium, polymer, polycarbonate, and/or steel. In embodiments including a kit, multiple bridges 20 may be included, the bridges 20 being made from different materials from one another. In this way, the user may select a bridge 20 based on a preferred material, such as to avoid an allergy, or discomfort caused by some materials to the specific user.

FIG. 5D illustrates a diagrammatic side view of a portion of the bridge 20 of FIG. 5A, and FIG. 5E illustrates a diagrammatic back view thereof. A height 504 of the bridge 20 is shown in FIG. 5D, and a width 506 of the bridge 20 (less the width of the inserts on either side of the bridge 20), a width 508 of the insert 402, and a height 510 of the insert 402 are shown in FIG. 5E.

The height 504 of the bridge 20 may be from 6.667 millimeters (mm) to 9.6 mm. The width 506 of the bridge 20, less the inserts, may be from 20.458 mm to 35.112 mm. The width 508 of the insert 402 may be from 4.167 mm to 6 mm. The height 510 of the insert 402 may be from 4.583 mm to 6.6 mm. As disclosed above, different bridges 20 may be present in a kit, and the different bridges 20 may each have different dimensions with respect to the height 504 of the bridge 20, the width 506 of the bridge 20 less the inserts, the width 508 of the inserts 402, and/or the height 510 of the inserts 402.

Additionally, the bridge 20 may have an angle of travel between the inserts 402. This angle of travel may be from 80 degrees to 144 degrees. Stated another way, the angle of travel may be from 1.396 radians to 2.513 radians.

Figure 6A:
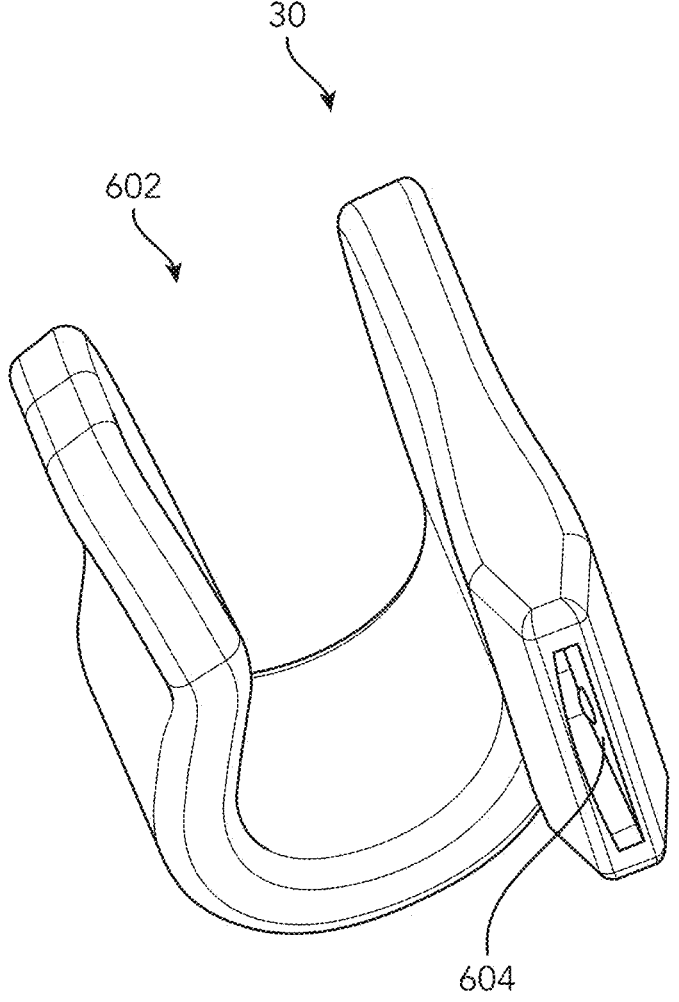
FIG. 6A illustrates a perspective view of an arm, according to some embodiments.
Figure 6B:
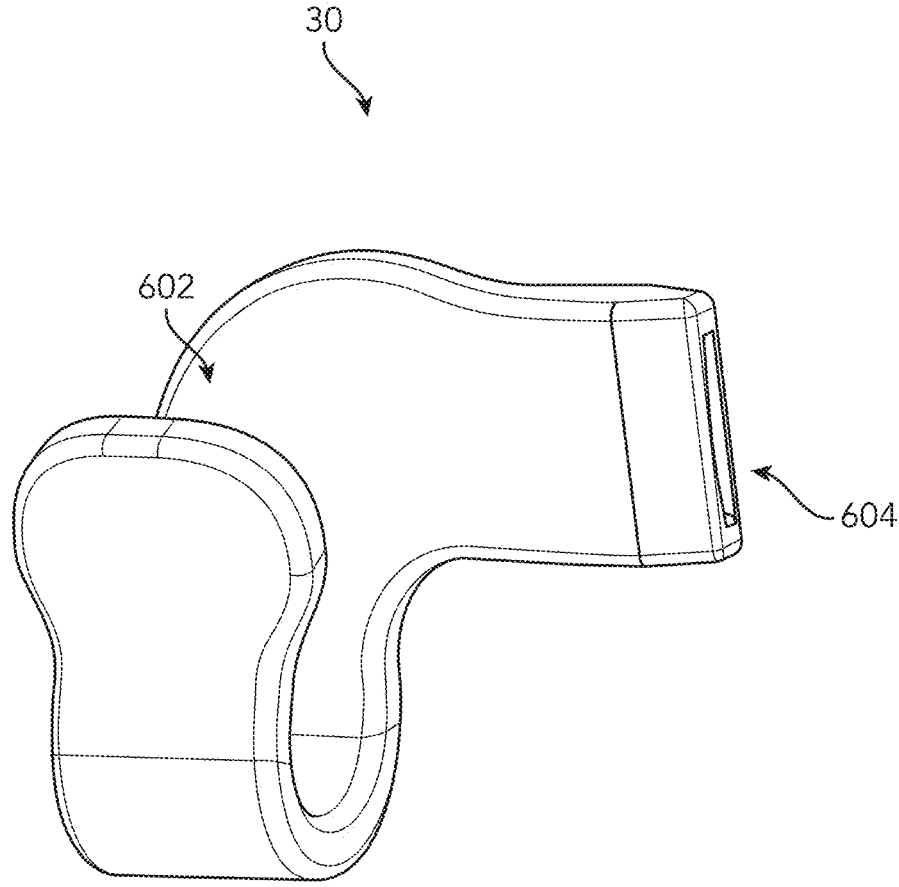
FIG. 6B illustrates a side view of the arm of FIG. 6A, according to some embodiments.
Figure 6C:
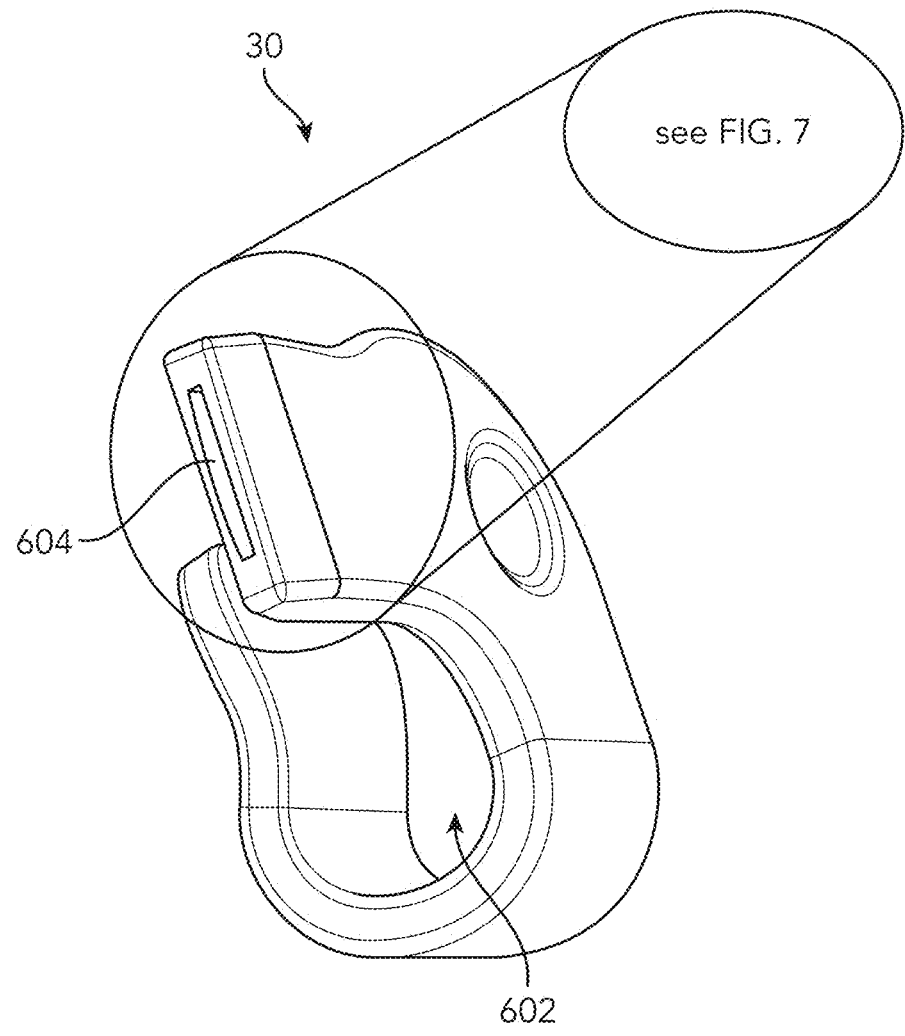
FIG. 6C illustrates a front view of the arm of FIG. 6A, according to some embodiments.
Figure 6D:
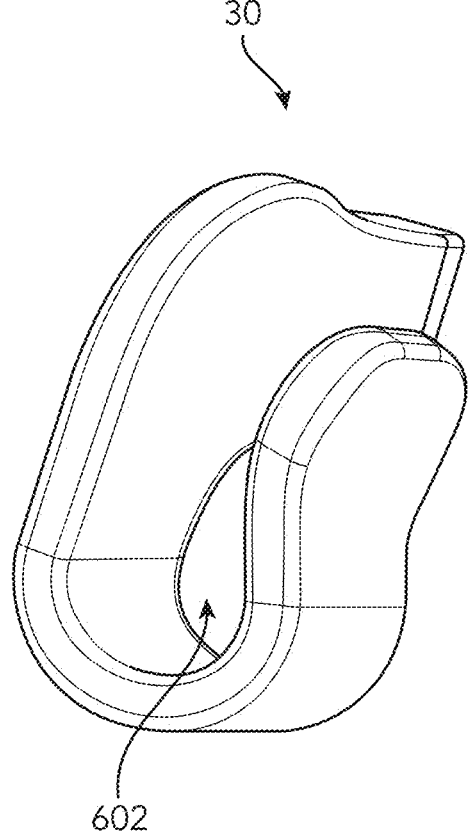
FIG. 6D illustrates a back view of the arm of FIG. 6A, according to some embodiments.
Figure 6E:
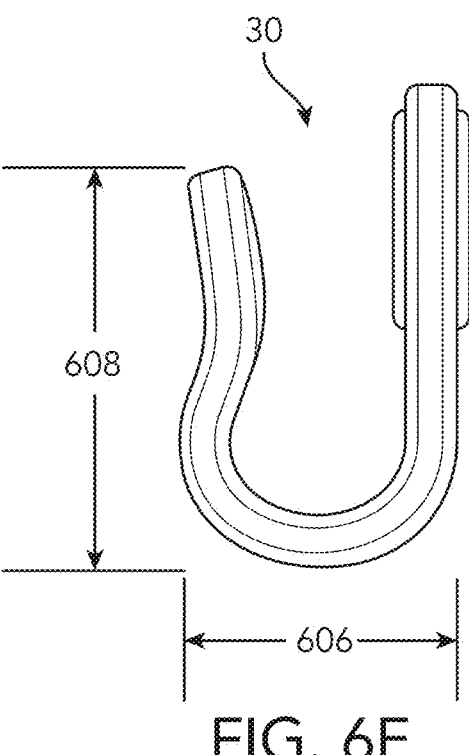
FIG. 6E illustrates a diagrammatic front view of the arm of FIG. 6A, according to some embodiments.
Figure 6F:
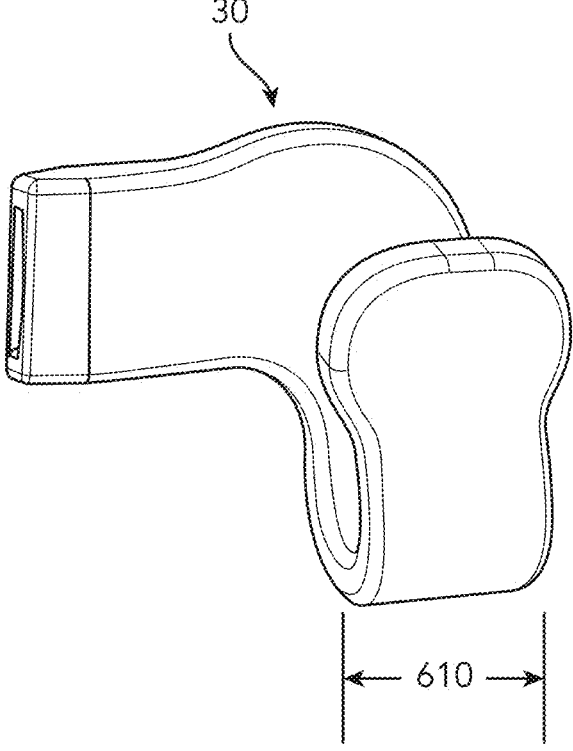
FIG. 6F illustrates a diagrammatic side view of the arm of FIG. 6A, according to some embodiments.

FIG. 6A illustrates a perspective view of an arm 30, according to some embodiments. FIG. 6B illustrates a side view, FIG. 6C illustrates a front view, and FIG. 6D illustrates a back view thereof. FIG. 6E illustrates a diagrammatic front view, and FIG. 6F illustrates a diagrammatic side view thereof. For illustration purposes, only one arm 30 is shown, as the opposing arm 30 may be identical, with the features mirrored. For the purposes of FIGS. 6A-6D, arm 30b from FIGS. 1-3C is illustrated and referred to here as arm 30.

As shown in FIGS. 6A-6D, the arm 30 may include a nasal coupling mechanism 602 and a slot 604. As described above with respect to FIGS. 4A-4C, the slot 604 may be configured to detachably couple with the inserts 402 on the bridge 20. For example, the slot 604 may be configured to receive at least a portion of an insert therewithin. The slot 604 may be of a height and width which interact with the inserts 402 of the bridge 20, such as to make a strong coupling, while not detracting from the ability to remove the arm 30 from the bridge 20.

The nasal coupling mechanism 602 may be sized and/or configured with respect to the width of an ala of a user's nose, as well as the depth of their nostril. In embodiments including a kit, multiple arms 30 may be included, the arms 30 including different combinations of height (e.g., the height 608 of an inner portion of the arm), which is inserted into the nostril, as well as the width of the opening (e.g., the space between inner portion 802 and outer portion 806 as shown and described in FIG. 8 below) for interacting with the user's alae. In this way, the user may select an arm 30 based on personal preference and/or comfort involving how far the arm 30 sits within their nose while in use, as well as how tightly the arm 30 presses against the user's alae while in use. Additionally, magnets may be provided within arms 30 to cause the nasal coupling mechanism 602 to hold more strongly to the user's alae. In additional or alternative embodiments, a portion of the arm 30 may include a magnetized material (e.g., steel, etc.) for interacting with a magnet in a different portion of the arm 30 to cause the nasal coupling mechanism 602 to hold more strongly to the user's alae.

Figure 8:
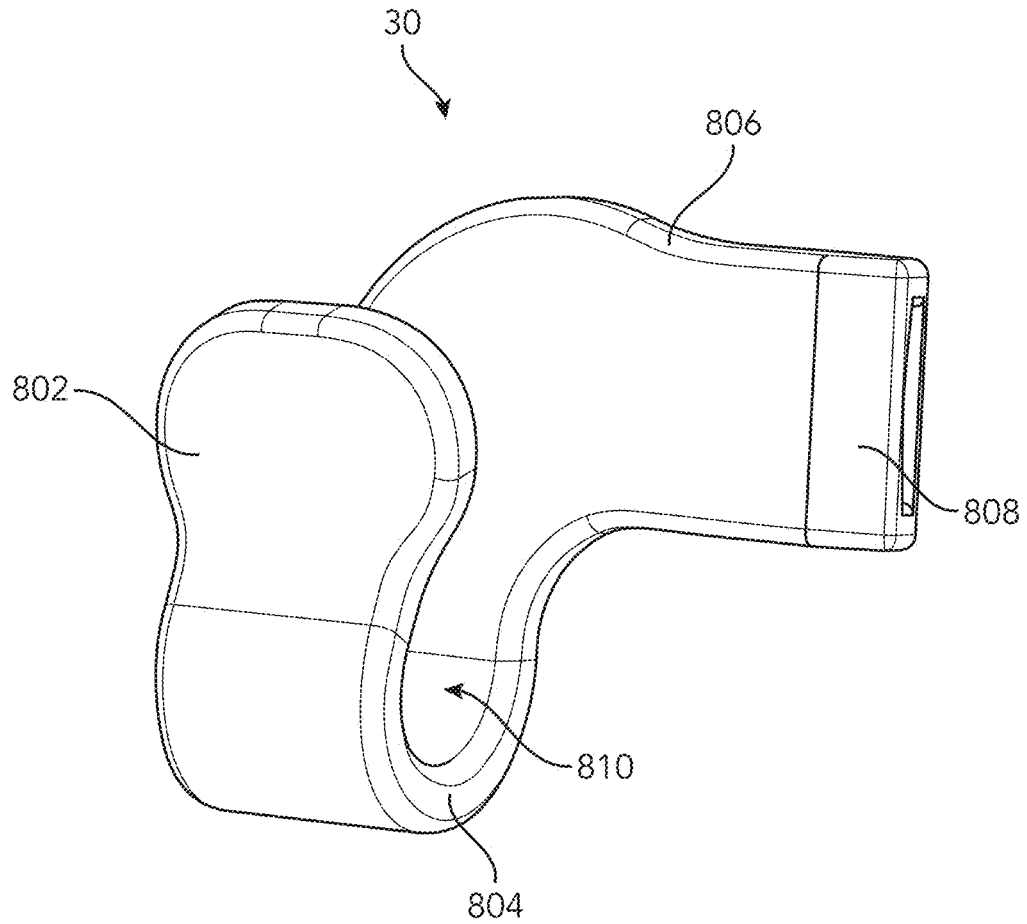
FIG. 8 illustrates a side view of an arm, according to some embodiments.

The arm includes four main portions—an "outer" portion, which, when in use, is disposed around or about the outside of the user's nose (dorsum), and includes the slot 604 for coupling the arm with the bridge (or is otherwise attached to a "coupling" portion), an "inner" portion, which, when in use, is disposed within the user's nose, and an "ala contacting" portion, which connects the outer portion to the inner portion, and, when in use, may at least partially rest upon the underside of the user's ala. FIG. 8 illustrates this in greater depth.

The length of the inner portion may be chosen, based on a selected arm 30, in order to provide an insertion depth that is comfortable for the user. The ala contacting portion may be chosen, based on a selected arm 30, in order to provide a width between the inner portion and the outer portion that fits about/is comfortable when placed about a user's ala. This may be determined by the user, as well as the width of the user's ala. For example dimensions of the arm 30, refer to FIGS. 6E and 6F below. In embodiments including magnets, the magnets may be disposed in the inner portion and/or the outer portion such that the inner portion magnet is attracted to the outer portion magnet about the tissue of the nose above the ala, thereby securing the arm to the user's nose.

The arms 30 may be formed from silicon, plastic, a combination of silicon and plastic, or polymer. In embodiments including a kit, multiple arms 30 may be included, the arms 30 being made from different materials from one another. In this way, the user may select an arm 30 based on a preferred material, such as to avoid an allergy, or discomfort caused by some materials to the specific user.

FIG. 6E illustrates a diagrammatic front view of the arm 30 of FIG. 6A, and FIG. 6F illustrates a diagrammatic side view thereof. A depth 606 of the arm 30 and a height 608 of an inner portion of the arm 30 (e.g., inner portion 802 as shown and described in FIG. 8 below) are shown in FIG. 6E, and a width 610 of an ala contacting portion of the arm 30 (e.g., ala contacting portion 804 as shown and described in FIG. 8 below) are illustrated in FIG. 6F.

The depth 606 of the arm 30 may be from 9.008 mm to 13.524 mm. The height 608 of the inner portion of the arm 30 may be from 12.983 mm to 20.592 mm. The width 610 of the ala contacting portion of the arm 30 may be from 6.75 mm to 9.72 mm. As disclosed above, different arms 30 may be present in a kit, and the different arms 30 may each have different dimensions with respect to the depth 606 of the arm 30, the height 608 of the inner portion of the arm 30, and the width 610 of the ala contacting portion of the arm 30.

Figure 7:
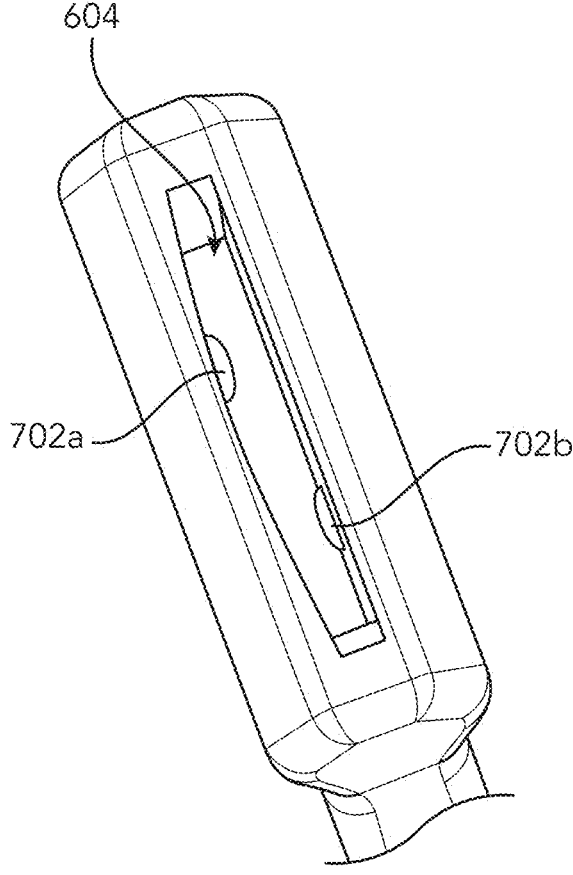
FIG. 7 illustrates a partial view of a slot of an arm, according to some embodiments.

FIG. 7 illustrates a partial view of a slot 604 of an arm 30, according to some embodiments. As seen within the slot 604, male coupling mechanisms 702 may be present and disposed about an inner surface of the slot 604.

As shown in FIG. 7, two male coupling mechanisms 702a and 702b are disposed within the slot 604. In alternate embodiments, one male coupling mechanism 702 is disposed within the slot 604. In further embodiments, a greater number than two male coupling mechanisms 702 are disposed within the slot 604. In still further embodiments, the number of male coupling mechanisms 702 within the slot 604 of the first arm 30a does not match the number of male coupling mechanisms 702 within the slot 604 of the second arm 30b. It may be desirable to align the number and positioning of male coupling mechanisms 702 with the number and positioning of the associated female coupling mechanisms 502.

The male coupling mechanisms 702 may be protrusions along a wall within the slot 604. In some embodiments, the male coupling mechanisms 702 match, or approximately match, the shape of the female coupling mechanisms 502. The male coupling mechanisms 702 may be configured to interact with the female coupling mechanisms 502 when the inserts 402 are coupled with the slot, so as to help at least partially maintain a coupling between the arm and the bridge. The male coupling mechanisms 702 may be configured to at least partially enter the female coupling mechanisms 502. According to some embodiments, some male coupling mechanisms 702 may reside on a wall of the slot opposite other male coupling mechanisms 702.

FIG. 8 illustrates a side view of an arm 30, according to some embodiments. FIG. 8 is presented to break down the specific portions of the arm 30. For example, an inner portion 802 is included. The inner portion 802 may be the portion of the arm 30 which is inserted into a user's nostril. The inner portion 802 is shown connected to an outer portion 806 via an ala contacting portion 804. In some embodiments, the ala contacting portion 804 curves about the ala of a user's nose.

According to some embodiments, the outer portion 806 makes contact with an exterior of the user's nose (dorsum). The outer portion 806 terminates in a coupling portion 808. The coupling portion 808 may be used to couple the arm 30 to the bridge 20, such as by way of the female coupling mechanisms as shown and described in FIG. 7 above.

Additionally, an opening 810 is illustrated between inner portion 802 and outer portion 806, about which the ala contacting portion 804 extends. The opening 810 may increase in width based on a force placed on either of the inner portion 802 and/or the outer portion 806 to permit a user to extend the arm 30 about their alae. An inherent spring constant of the arm 30 material may permit the arm to snugly fit upon the user's alae.

Figure 9:
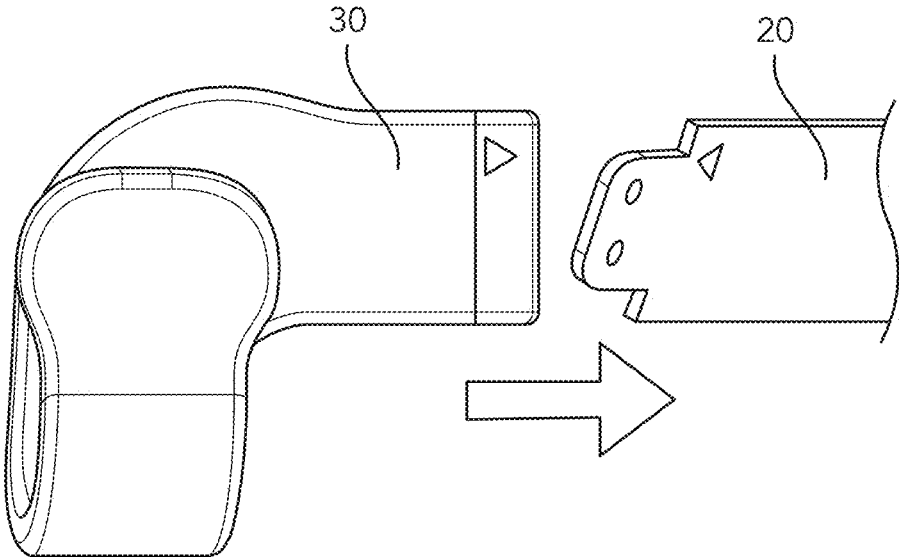
FIG. 9 illustrates a diagrammatic back view of a nasal dilating device being put together, according to some embodiments.

FIG. 9 illustrates a diagrammatic back view of a nasal dilating device 10 being put together, according to some embodiments. As shown, the arm 30 may be placed onto the bridge 20, or, stated another way, a portion of the bridge 20 may be inserted into the arm 30 by way of the female coupling mechanisms and male coupling mechanisms as shown and described above.

Figure 10A:
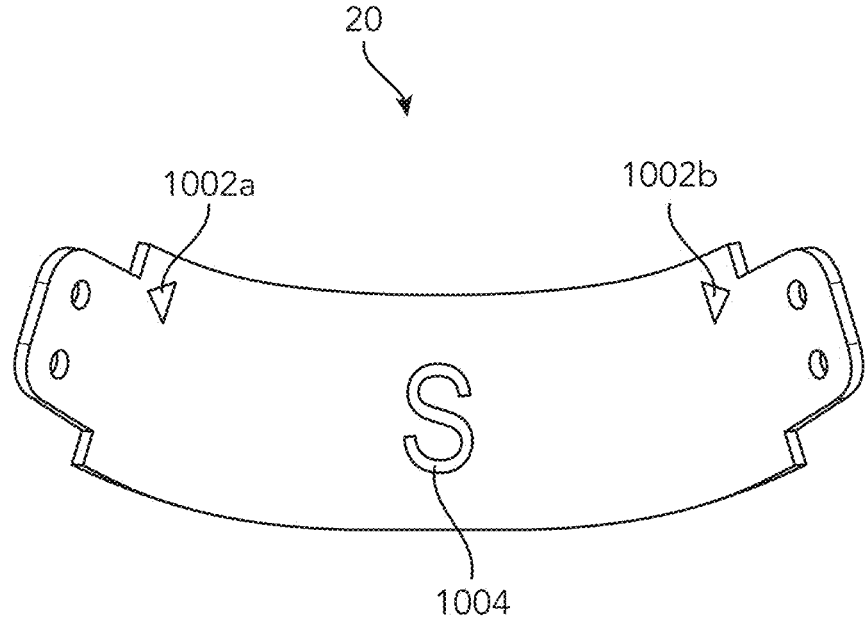
FIG. 10A illustrates a back view of a bridge, according to some embodiments.

FIG. 10A illustrates a back view of a bridge 20, according to some embodiments. As seen in FIG. 10A, bridge position indicators 1002a and 1002b are present. Bridge positioner indicators 1002a, 1002b may be used to indicate to a user how to orient the bridge 20 in order to couple the bridge 20 to the arms 30. The bridge position indicators 1002a, 1002b may be positioned and oriented such that they align with an arm position indicator (e.g., arm position indicator 1006 as shown and described in FIG. 10B below) when correctly oriented. The bridge position indicators 1002a, 1002b may be location-specific based on the left and right arms 30. The bridge position indicators 1002a, 1002b are illustrated as triangles in FIG. 10A. In additional or alternate embodiments, any shape may be used. However, it may be preferable to use a shape that has a corner that more obviously points in a direction, such as a triangle, a diamond, etc., in order to better orient the bridge 30 with the arms 30.

Also shown in FIG. 10A, a bridge size indicator 1004 appears as a letter "S" on a back surface of the bridge 20. The bridge size indicator 1004 may indicate to a user what size the bridge 20 is. An "S" is used here to indicate "small." In this theme, indicators such as "2XS," "XXS," "XS," "M," "L," "XL," "XXL," "2XL," and other variants may also be used to indicate various different sizes for a respective bridge. In additional or alternate embodiments, the bridge size indicator 1004 may be a numeric indicator such as the numbers one through five, with one being the smallest size and five being the largest size, or vice versa. The numeric indicators could be spelled out, or shown as Arabic numerals. In additional or alternate embodiments, the bridge size indicator 1004 may be a shape, such as a circle, square, triangle, etc., where the relational size of the shape between different bridges 20 indicates the relational size of the bridges 20 themselves.

Figure 10B:
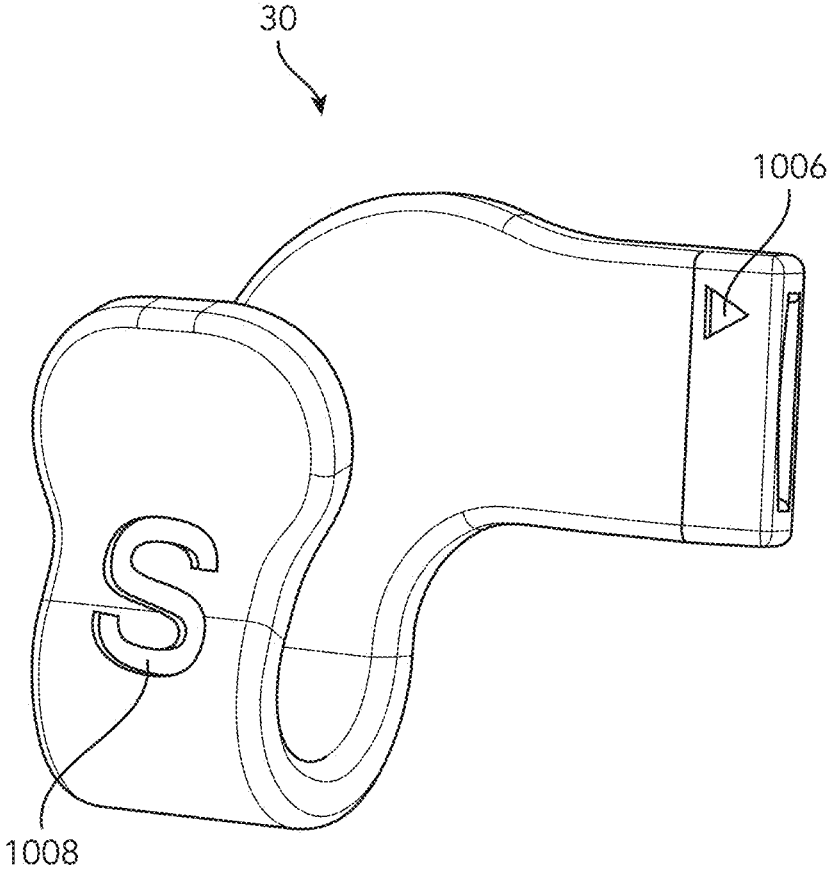
FIG. 10B illustrates a side view of an arm, according to some embodiments.

FIG. 10B illustrates a side view of an arm 30, according to some embodiments. As seen in FIG. 10B, an arm position indicator 1006 is present. Arm position indicator 1006 may be used to indicate to a user how to orient the arm 30 in order to couple the arm 30 to the bridge 20. The arm position indicator 1006 may be positioned and oriented such that it aligns with the bridge position indicator 1002a or 1002b when correctly oriented. The arm position indicator 1006 is illustrated as a triangle in FIG. 10B. In additional or alternate embodiments, any shape may be used. However, it may be preferable to use a shape that has a corner that more obviously points in a direction, such as a triangle, a diamond, etc., in order to better orient the arm 30 with the bridge 20.

Also shown in FIG. 10B, an arm size indicator 1008 appears as a letter "S" on the inner portion of the arm 30 (e.g., inner portion 802 in FIG. 8 above). The arm size indicator 1008 may indicate to a user what size the arm 30 is. An "S" is used here to indicate "small." In this theme, indicators such as "2XS," "XXS," "XS," "M," "L," "XL," "XXL," "2XL," and other variants may also be used to indicate various different size for a respective arm. In additional or alternate embodiments, the arm size indicator 1008 may be a numeric indicator such as the numbers one through five, with one being the smallest size and five being the largest size, or vice versa. The numeric indicators could be spelled out, or shown as Arabic numerals. In additional or alternate embodiments, the arm size indicator 1008 may be a shape, such as a circle, square, triangle, etc., where the relational size of the shape between different arms 30 indicates the relational size of the arms 30 themselves.

Figure 11A:
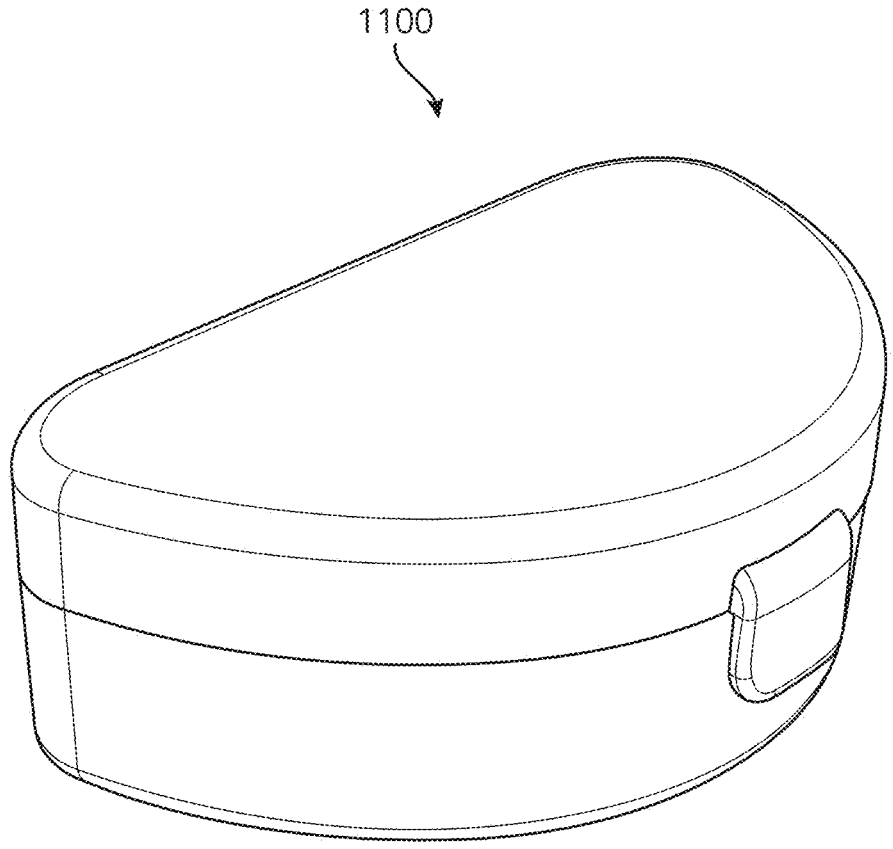
FIG. 11A illustrates a perspective view of a case, according to some embodiments.

FIG. 11A illustrates a perspective view of a case 1100, according to some embodiments. In embodiments including a kit, a case 1100 may be provided. The case 1100 may be a carrying case. The case may be sized and configured to hold multiple bridges 20 and arms 30, in any combination as described above, to facilitate a user in storing their devices and finding specific components for customizing their devices. The case 1100 may be made from plastic (such as transparent plastic, translucent plastic, opaque plastic, colored plastic, etc.), plastic and foam, faux fur, nylon, or combinations thereof.

Figure 11B:
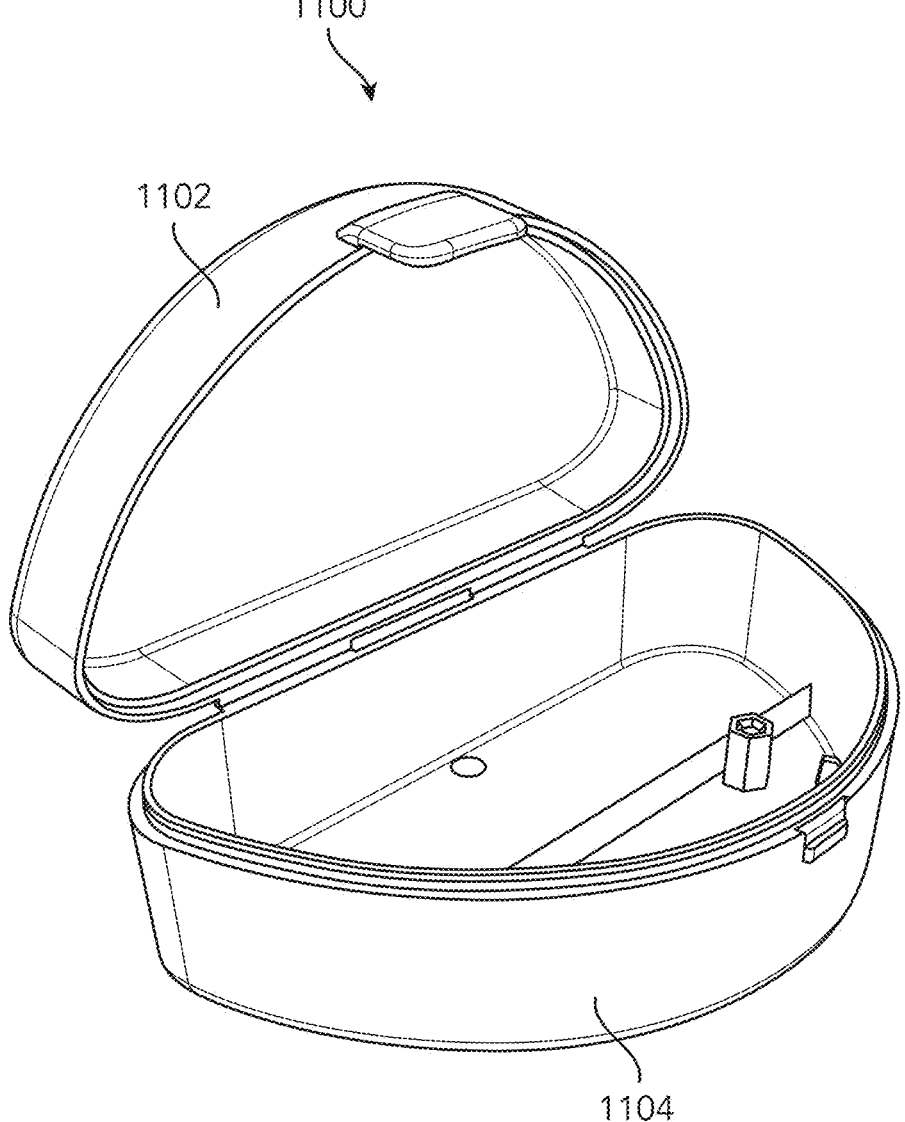
FIG. 11B illustrates a perspective view of the case of FIG. 11A in an open configuration, according to some embodiments.

FIG. 11B illustrates a perspective view of the case 1100 of FIG. 11A in an open configuration, according to some embodiments. In some embodiments, the case 1100 includes a hinge such that the case 1100 can be opened without individual pieces separating from one another. When opened, the case 1100 can be distinguished as a lid 1102 and a container 1104. In additional or alternative embodiments, the case 1100 may not include a hinge, and instead include a separate lid 1102 and container 1104. In such embodiments, the lid 1102 and the container 1104 may couple to one another when in a closed configuration through a snap fit, a friction fit, etc.

Figure 11C:
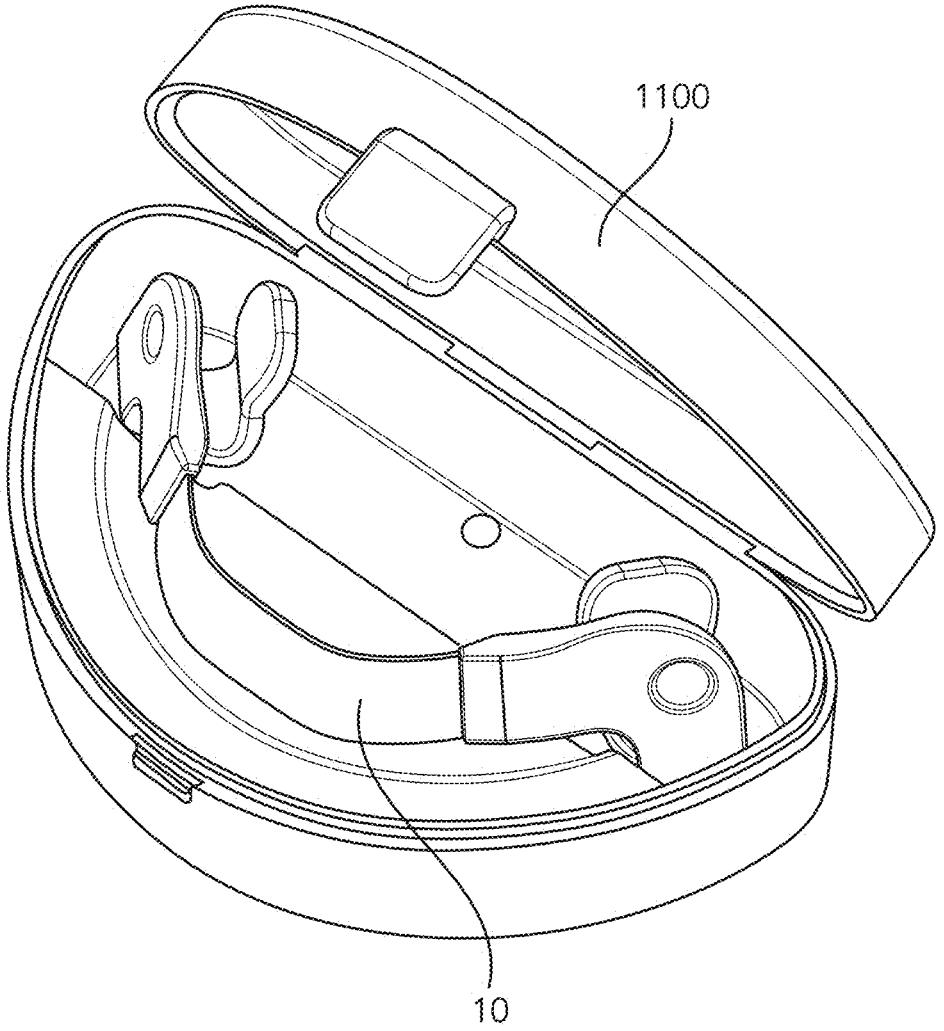
FIG. 11C illustrates a perspective view of the case of FIG. 11A in an open configuration with a nasal opening device inside, according to some embodiments.

FIG. 11C illustrates a perspective view of the case 1100 of FIG. 11A in an open configuration with a nasal dilating device 10 inside, according to some embodiments. The embodiment illustrated in FIG. 11C shows a case 1100 sized and configured to accept a single nasal dilating device 10 in order to minimize the footprint of the case 1100. In additional or alternative embodiments, the case 1100 may be larger so as to permit the carriage of a greater number of nasal dilating devices 10, to permit size customization on the go.

Figure 11D:
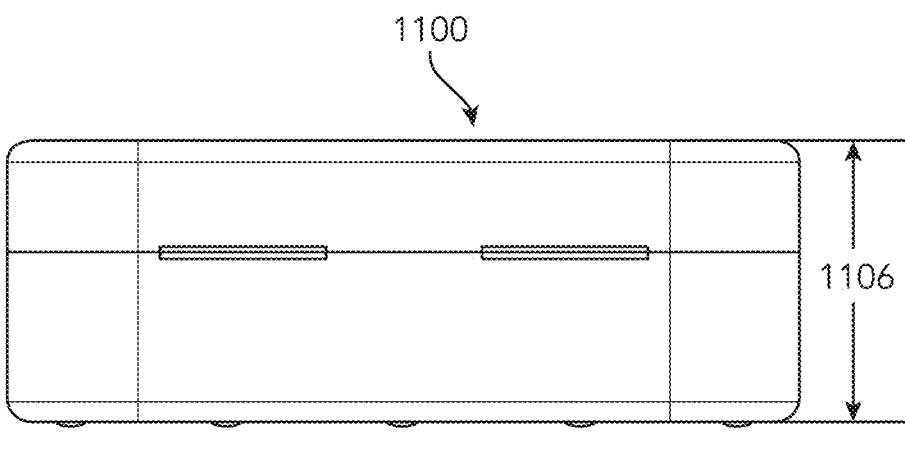
FIG. 11D illustrates a diagrammatic front view of the case of FIG. 11A, according to some embodiments.
Figure 11E:
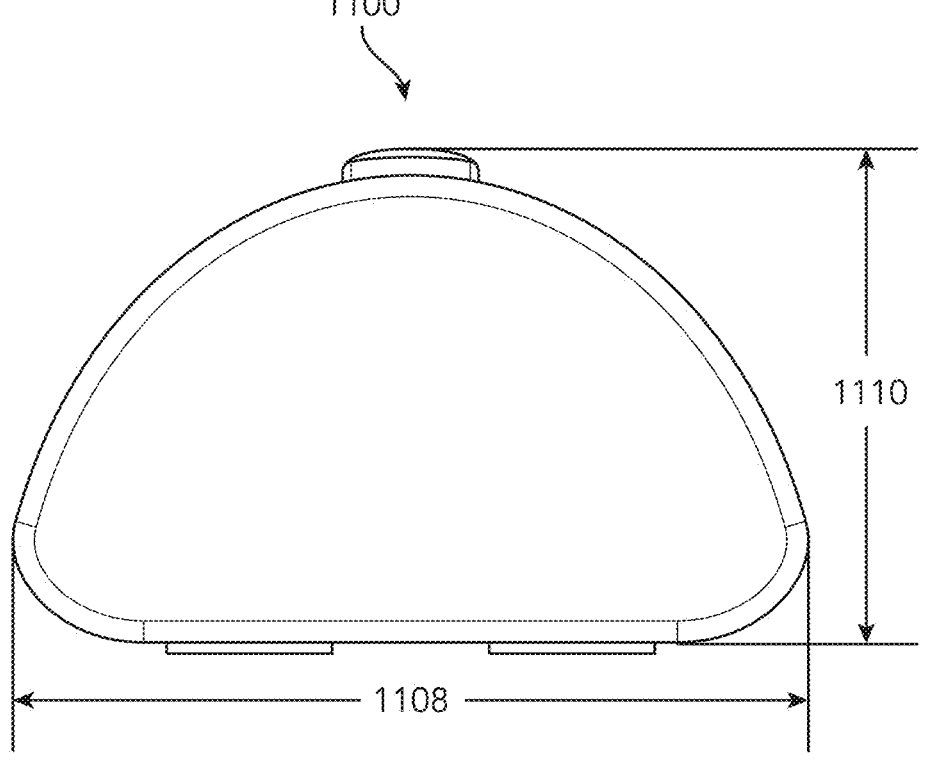
FIG. 11E illustrates a diagrammatic top view of the case of FIG. 11A, according to some embodiments.

FIG. 11D illustrates a diagrammatic front view of the case 1100 of FIG. 11A, and FIG. 11E illustrates a diagrammatic top view thereof. A height 1106 of the case 1100 is shown in FIG. 11D, and a length 1108 of the case 1100 and a width 1110 of the case 1100 are shown in FIG. 11E.

The height 1106 of the case 1100 may be from 20.758 mm to 29.892 mm. The length 1108 of the case 1100 may be from 59.608 mm to 85.836 mm. The width 1110 of the case 1100 may be from 34.675 mm to 49.932 mm.

Figure 12:
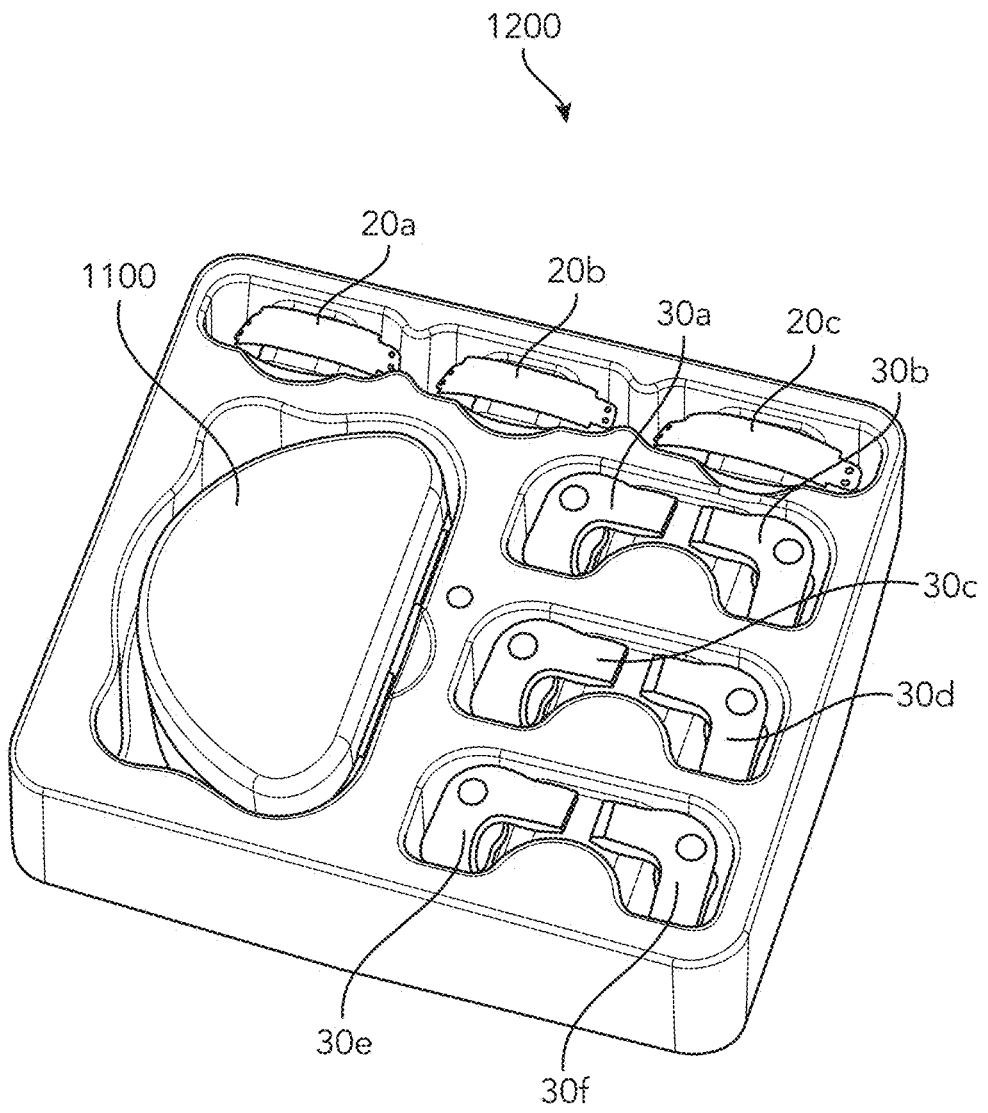
FIG. 12 illustrates a packing tray, according to some embodiments.

FIG. 12 illustrates a packing tray 1200, according to some embodiments. As shown in FIG. 12, the packing tray 1200 may include cavities for receiving the multiple parts of a kit. Specifically illustrated are a case 1100, bridges 20*a*, 20*b*, and 20*c*, and arms 30*a*, 30*b*, 30*c*, 30*d*, 30*e*, and 30*f*. In additional or alternate embodiments, the packing tray may be larger, so as to hold additional cases 1100, bridges 20, and/or arms 30, or the packing tray may be smaller, so as to hold fewer bridges 20 and/or arms 30, or to exclude the case 1100.

Some of the components listed herein use the same number from figure to figure. It should be appreciated that these components use the same numbers solely for ease of reference and to facilitate comprehension for the reader. While these components may use the same numbers, differences may be present in these components as illustrated in the various figures in which they appear and as described in the specification herein.

None of the steps described herein is essential or indispensable. Any of the steps can be adjusted or modified. Other or additional steps can be used. Any portion of any of the steps, processes, structures, and/or devices disclosed or illustrated in one embodiment, flowchart, or example in this specification can be combined or used with or instead of any other portion of any of the steps, processes, structures, and/or devices disclosed or illustrated in a different embodiment, flowchart, or example. The embodiments and examples provided herein are not intended to be discrete and separate from each other.

The section headings and subheadings provided herein are nonlimiting. The section headings and subheadings do not represent or limit the full scope of the embodiments described in the sections to which the headings and subheadings pertain. For example, a section titled "Topic 1" may include embodiments that do not pertain to Topic 1 and embodiments described in other sections may apply to and be combined with embodiments described within the "Topic 1" section.

The various features and processes described above may be used independently of one another, or may be combined in various ways. All possible combinations and subcombinations are intended to fall within the scope of this disclosure. In addition, certain method, event, state, or process blocks may be omitted in some implementations. The methods, steps, and processes described herein are also not limited to any particular sequence, and the blocks, steps, or states relating thereto can be performed in other sequences that are appropriate. For example, described tasks or events may be performed in an order other than the order specifically disclosed. Multiple steps may be combined in a single block or state. The example tasks or events may be performed in serial, in parallel, or in some other manner. Tasks or events may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to each be present.

The term "and/or" means that "and" applies to some embodiments and "or" applies to some embodiments. Thus, A, B, and/or C can be replaced with A, B, and C written in one sentence and A, B, or C written in another sentence. A, B, and/or C means that some embodiments can include A and B, some embodiments can include A and C, some embodiments can include B and C, some embodiments can only include A, some embodiments can include only B, some embodiments can include only C, and some embodiments can include A, B, and C. The term "and/or" is used to avoid unnecessary redundancy.

The term "substantially" refers to less than or equal to $+/-1\%$, $+/-2\%$, $+/-3\%$, $+/-4\%$, $+/-5\%$, $+/-6\%$, $+/-7\%$, $+/-8\%$, $+/-9\%$, $+/-10\%$, $+/-11\%$, $+/-12\%$, $+/-14\%$, or $+/-15\%$ variation. As a non-limiting example, substantially parallel represents a range of $-1$ to $1$ degree difference, $-5$ to $5$ degree difference, or $-15$ degrees to $15$ degrees of difference from being parallel, depending on the embodiments.

While certain example embodiments have been described, these embodiments have been presented by way of example only, and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein.

We claim:

1. A device, comprising:

a bridge comprising a first end and a second end opposite the first end, the bridge configured to be placed about the bridge of a nose of a user;

wherein the first end of the bridge comprises a first insert comprising a first female coupling mechanism, and wherein the second end of the bridge comprises a second insert comprising a second female coupling mechanism, a first arm configured to interact with the first end so as to be detachably coupled to the first end, wherein at least a portion of the first arm is configured to be inserted within the nose; and a second arm configured to interact with the second end so as to be detachably coupled to the second end, wherein at least a portion of the second arm is configured to be inserted within the nose, wherein the device is configured to detachably couple with a nose of a user, and wherein the bridge comprises a spring constant, such that the bridge is configured to independently pull the first arm and the second arm away from one another to thereby open a nasal airway.

2. The device of claim 1, wherein the bridge is configured to change in width by about five millimeters when in use.

3. The device of claim 1, wherein the bridge comprises i) stainless steel, ii) high-precision phosphorus copper, iii) titanium, iv) polymer, v) polycarbonate, vi) steel, or vii) combinations thereof.

4. The device of claim 1, wherein the first arm and the second arm each comprise i) silicon, ii) plastic, iii) polymer, or iv) combinations thereof.

5. The device of claim 1, wherein the first arm comprises a first nasal coupling mechanism, wherein the second arm comprises a second nasal coupling mechanism, wherein the first nasal coupling mechanism is configured to detachably couple the first arm to a first ala of the nose, and wherein the second nasal coupling mechanism is configured to detachably couple the second arm to a second ala of the nose.

6. The device of claim 5, further comprising:

a first pair of magnets disposed in the first nasal coupling mechanism, the first pair of magnets configured to detachably couple the first arm to the first ala; and a second pair of magnets disposed in the second nasal coupling mechanism, the second pair of magnets configured to detachably couple the second arm to the second ala.

7. The device of claim 1, wherein the device is configured to apply pressure to nostrils of the nose, thereby opening a nasal airway.

8. The device of claim 1, wherein the bridge comprises a bridge position indicator, the first arm comprises a first arm position indicator, and the second arm comprises a second arm position indicator, wherein the bridge position indicator and the first arm position indicator are configured to align the bridge with the first arm, and wherein the bridge position indicator and the second arm position indicator are configured to align the bridge with the second arm.

9. The device of claim 8, wherein i) the bridge position indicator, ii) the first arm position indicator, iii) the second arm position indicator, or iv) combinations thereof are triangular.

10. The device of claim 1, wherein i) each of the first arm and the second arm comprise an arm size indicator, ii) the bridge comprises a bridge size indicator, or iii) both.

11. The device of claim 1, wherein i) a height of the bridge is from 6.667 millimeters (mm) to 9.6 mm, ii) a width of the bridge, less the first insert and the second insert, is from 20.458 mm to 35.112 mm, iii) an angle of travel of the bridge is from 80 degrees to 144 degrees, or iv) combinations thereof.

12. The device of claim 1, wherein a) a width of i) the first insert, ii) the second insert, or iii) both is from 4.167 mm to 6 mm, b) a height of i) the first insert, ii) the second insert, or iii) both is from 4.583 mm to 6.6 mm, or c) combinations thereof.

13. The device of claim 1, wherein i) a depth of either the first arm, the second arm, or both is from 9.008 mm to 13.524 mm, ii) a height of an inner portion of either the first arm, the second arm, or both is from 12.983 mm to 20.592 mm, iii) a width of an ala contacting portion of either the first arm, the second arm, or both is from 6.75 mm to 9.72 mm, or iv) combinations thereof.

14. The device of claim 1, wherein each of the first arm and the second arm comprise an inherent spring constant configured to couple each of the first arm and the second arm to an ala of a user's nose.

15. A device, comprising:

a bridge comprising a first end and a second end opposite the first end, the bridge configured to be placed about the bridge of a nose of a user;

wherein the first end of the bridge comprises a first insert, and wherein the second end of the bridge comprises a second insert, a first arm configured to interact with the first end so as to be detachably coupled to the first end, wherein at least a portion of the first arm is configured to be inserted within the nose, and wherein the first arm comprises a first slot; and a second arm configured to interact with the second end so as to be detachably coupled to the second end, wherein at least a portion of the second arm is configured to be inserted within the nose, and wherein the second arm comprises a second slot, wherein the device is configured to detachably couple with a nose of a user, and wherein the bridge comprises a spring constant, such that the bridge is configured to independently pull the first arm and the second arm away from one another to thereby open a nasal airway.

16. The device of claim 15, wherein the first slot is configured to detachably couple with the first insert, and wherein the second slot is configured to detachably couple with the second insert.

17. The device of claim 15, further comprising:

a first male coupling mechanism disposed within the first slot; and a second male coupling mechanism disposed within the second slot.

18. The device of claim 17, wherein the first male coupling mechanism is configured to detachably couple with a first female coupling mechanism when the first slot is coupled with the first insert or first end, and wherein the second male coupling mechanism is configured to detachably couple with a second female coupling mechanism when the second slot is coupled with the second insert or second end.

19. The device of claim 15, wherein the device is configured to apply pressure to nostrils of the nose, thereby opening a nasal airway.

20. The device of claim 15, wherein i) each of the first arm and the second arm comprise an arm size indicator, ii) the bridge comprises a bridge size indicator, or iii) both.

\*    \*    \*    \*    \*